(12) United States Patent
Pedersen et al.

(10) Patent No.: US 8,114,833 B2
(45) Date of Patent: *Feb. 14, 2012

(54) PROPYLENE GLYCOL-CONTAINING PEPTIDE FORMULATIONS WHICH ARE OPTIMAL FOR PRODUCTION AND FOR USE IN INJECTION DEVICES

(75) Inventors: Tina Bjeldskov Pedersen, Smørum (DK); Claude Bonde, Lyngby (DK); Dorthe Kot Engelund, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 663 days.

This patent is subject to a terminal disclaimer.

(21) Appl. No.: 11/435,977

(22) Filed: May 17, 2006

(65) Prior Publication Data

US 2007/0010424 A1 Jan. 11, 2007

Related U.S. Application Data

(63) Continuation of application No. PCT/DK2004/000792, filed on Nov. 18, 2004.

(60) Provisional application No. 60/524,653, filed on Nov. 24, 2003.

(30) Foreign Application Priority Data

Nov. 20, 2003 (DK) .................. 2003 01719

(51) Int. Cl.
*A61K 38/26* (2006.01)

(52) U.S. Cl. .......................... 514/2; 530/308

(58) Field of Classification Search .................. None
See application file for complete search history.

(56) References Cited

U.S. PATENT DOCUMENTS

| | | | |
|---|---|---|---|
| 4,468,346 A | 8/1984 | Paul et al. | |
| 5,206,219 A | 4/1993 | Desai | |
| 5,272,135 A | 12/1993 | Takruri | |
| 5,455,331 A | 10/1995 | Pearce | |
| 5,652,216 A | 7/1997 | Kornfelt et al. | |
| 5,705,483 A | 1/1998 | Galloway | |
| 6,133,229 A | 10/2000 | Gibson et al. | |
| 6,184,201 B1 | 2/2001 | Drucker et al. | |
| 6,268,343 B1 | 7/2001 | Knudsen et al. | |
| 6,274,553 B1 | 8/2001 | Furuya | |
| 6,284,727 B1 | 9/2001 | Kim et al. | |
| 6,380,357 B2 | 4/2002 | Hermeling | |
| 6,384,016 B1 | 5/2002 | Kaarsholm | |
| 6,444,788 B1 | 9/2002 | Staby | |
| 6,586,399 B1 | 7/2003 | Drucker et al. | |
| 6,844,321 B2 | 1/2005 | Arentsen | |
| 7,022,674 B2 | 4/2006 | DeFelippis et al. | |
| 7,049,284 B2 | 5/2006 | Drucker et al. | |
| 7,056,886 B2 | 6/2006 | Isaacs | |
| 7,238,663 B2 | 7/2007 | DeFelippis et al. | |
| 2001/0014666 A1 | 8/2001 | Hermeling et al. | |
| 2001/0027180 A1 | 10/2001 | Isaacs | |
| 2002/0151467 A1 | 10/2002 | Leung | |
| 2003/0060412 A1 | 3/2003 | Prouty, et al. | |
| 2003/0069182 A1 | 4/2003 | Rinella | |
| 2003/0119734 A1 | 6/2003 | Flink et al. | |
| 2003/0158101 A1 | 8/2003 | Drucker | |
| 2003/0207802 A1 | 11/2003 | DeFelippis | |
| 2003/0220243 A1 | 11/2003 | Glaesner et al. | |
| 2003/0220255 A1 | 11/2003 | Knudsen et al. | |
| 2004/0156835 A1 | 8/2004 | Imoto et al. | |
| 2004/0248782 A1 | 12/2004 | Bridon et al. | |
| 2006/0084605 A1 * | 4/2006 | Engelund et al. ............... 514/12 |
| 2006/0287221 A1 * | 12/2006 | Knudsen et al. .................. 514/3 |

FOREIGN PATENT DOCUMENTS

| | | |
|---|---|---|
| CA | 2306024 | 4/1999 |
| CA | 2527743 | 12/2004 |
| EP | 0431679 | 11/1990 |
| EP | 0438767 | 12/1990 |
| EP | 699687 | 8/1995 |
| EP | 708179 | 4/1996 |
| EP | 747390 | 12/1996 |
| EP | 0926159 | 6/1999 |
| EP | 1329462 | 10/2001 |
| EP | 1424077 | 5/2002 |
| EP | 1344533 | 9/2003 |
| EP | 1396499 | 3/2004 |
| EP | 722492 | 3/2005 |
| JP | 10101696 | 4/1998 |
| JP | 2000-510813 | 8/2000 |
| JP | 2001-525371 | 12/2001 |
| JP | 2002-504908 | 2/2002 |
| JP | 2002-508332 | 3/2002 |
| JP | 2002-524514 | 8/2002 |
| JP | 2002-532557 | 10/2002 |
| JP | 2003-519195 | 6/2003 |
| JP | 2003519195 | 6/2003 |

(Continued)

OTHER PUBLICATIONS

Singh, S et al—Aaps Pharmscitech—2003—vol. 4—Part 3-pp. 334-342.

(Continued)

*Primary Examiner* — Christina Bradley
(74) *Attorney, Agent, or Firm* — Michael J. Brignati

(57) ABSTRACT

The present invention relates to pharmaceutical formulations comprising a peptide and propylene glycol, to methods of preparing such formulations, and to uses of such formulations in the treatment of diseases and conditions for which use of the peptide contained in such formulations is indicated. The present invention further relates to methods for reducing the clogging of injection devices by a peptide formulation and for reducing deposits on production equipment during production of a peptide formulation.

31 Claims, 7 Drawing Sheets

FOREIGN PATENT DOCUMENTS

| | | |
|---|---|---|
| PA | 200101010 | 6/2001 |
| RU | 2180218 | 3/2002 |
| WO | WO 9000200 | 1/1990 |
| WO | 92/19260 | 11/1992 |
| WO | 9318785 | 9/1993 |
| WO | WO 93/18785 | 9/1993 |
| WO | 93/23010 | 11/1993 |
| WO | 95/22560 | 2/1995 |
| WO | 95/05848 | 3/1995 |
| WO | WO 9510605 | 4/1995 |
| WO | 95/13825 | 5/1995 |
| WO | WO 96/20005 | 7/1996 |
| WO | 9624369 | 8/1996 |
| WO | WO 9638469 | 12/1996 |
| WO | WO 98/08871 | 3/1998 |
| WO | WO 98/31386 | 7/1998 |
| WO | 9856406 | 12/1998 |
| WO | 99/16417 | 4/1999 |
| WO | WO 9921889 | 5/1999 |
| WO | WO 99/29336 | 6/1999 |
| WO | WO 99/30731 | 6/1999 |
| WO | WO 99/43341 | 9/1999 |
| WO | WO 99/43708 | 9/1999 |
| WO | WO 9943707 | 9/1999 |
| WO | WO 00/15224 | 3/2000 |
| WO | WO 00/37098 | 6/2000 |
| WO | WO 00/41546 | 7/2000 |
| WO | WO 00/55119 | 9/2000 |
| WO | 0100223 | 1/2001 |
| WO | WO 01/43762 | 6/2001 |
| WO | 0151071 | 7/2001 |
| WO | WO 01/49314 | 7/2001 |
| WO | WO 01/51071 | 7/2001 |
| WO | WO 0152937 | 7/2001 |
| WO | WO 0155213 | 8/2001 |
| WO | WO 01/77141 | 10/2001 |
| WO | 02/67989 | 1/2002 |
| WO | 0247716 | 6/2002 |
| WO | WO 02/47715 | 6/2002 |
| WO | WO 02/48183 | 6/2002 |
| WO | WO 0248183 | 6/2002 |
| WO | 02098445 | 12/2002 |
| WO | 03/013589 | 2/2003 |
| WO | WO 03/020201 | 3/2003 |
| WO | WO 03/002136 | 4/2003 |
| WO | WO 03/035099 | 5/2003 |
| WO | WO 2004/029076 | 4/2004 |
| WO | WO 2004105781 | 12/2004 |
| WO | WO 2005/000222 | 1/2005 |
| WO | 2005/046716 | 5/2005 |
| WO | WO 2006/025882 | 3/2006 |

OTHER PUBLICATIONS

Non-Final Office Action mailed Dec. 9, 2009 in U.S. Appl. No. 12/184,531 filed Aug. 1, 2008 by Mortensen et al.
Sigma, Custom Peptide Synthesis, 2004, pp. 1-2, http://www.SIGMA-GENOSYS.COM/PEPTIDE_DESIGN.ASP.
Bailey et al. The Kinetics of Enzyme-Catalysed Reactions Biochemical Engineering Fundamentals, 2nd Ed., pp. 129-148 (1986).
Entry for Glycerin in Drugs.Com (www.Drugs.Com/PPA/glycerin-glycerol.html), Printed Aug. 04, 2009.
European Pharmacopoeia, 2007, vol. 1, p. 730, Council of Europe-Strasbourg.
S.E. Bondos & A. Bicknell, Detection and Prevention of Protein Aggregation Before During and After Purification, Analytical Biochemistry, 2003, 223-231, vol. 316, Academic Press.
Shinotesuto, Patent Abstracts of Japan, of JP10101696.
Skovgaard et al., "Using Evolutionary Information and Ancestral Sequences to Understand the Sequence-Function Relationship in GLP-1 Agonists," J. Mol. Bio., 2006, vol. 363, p. 977-988.
Tsoka et al, Selective Flocculation Ands Precipitation for the Improvement of Virus-Like Particle Recovery From Yeast Homogenate, Biotechnol Prog. vol. 16(4), pp. 661-7 (2000).
Non-Final Office Action in U.S. Appl. No. 10/185,923, Filed June 27, 2002, Inventors: Funk et al. Sent Mar. 10, 2006.
Non-Final Office Action in U.S. Appl. No. 10/185,923, Filed Jun. 27, 2002, Inventors: Flink et al. Sent Oct. 9, 2007.
Non-Final Office Action in U.S. Appl. No. 11/786,095, Filed Apr. 11,2007, Inventors: Funk et al. Sent Feb. 24, 2009.
Non-Final Office Action in U.S. Appl. No. 12/343,722, Filed Dec. 24, 2008, Inventors: Funk et al. Sent May 22, 2009.
Non-Final Office Action in U.S. Appl. No. 10/719,601, Filed Nov. 21, 2003, Inventors: Markussen et al. Sent Mar. 4, 2005.
Non-Final Office Action in U.S. Appl. No. 11/220,266, Filed Sep. 6, 2005, Inventors: Markussen et al. Sent Sep. 14, 2006.
Non-Final Office Action in U.S. Appl. No. 11/220,266, Filed Sep. 6, 2005, Inventors: Markussen et al. Sent Feb. 11, 2008.
Non-Final Office Action in U.S. Appl. No. 11/220,266, Filed Sep. 6, 2005, Inventors: Markussen et al. Sent Oct. 1, 2007.
Non-Final Office Action in U.S. Appl. No. 11/290,634, Filed Nov. 30, 2005, Inventors: Juul-Mortensen et al. Sent Jun. 30, 2008.
Non-Final Office Action in U.S. Appl. No. 11/290,634, Filed Nov. 30, 2005, Inventors: Juul-Mortensen et al. Sent Nov. 9, 2007.
Non-Final Office Action in U.S. Appl. No. 11/290,635, Filed Nov. 30, 2005, Inventors: Juul-Mortensen et al. Sent Feb. 2, 2007.
Non-Final Office Action in U.S. Appl. No. 11/290,635, Filed Nov. 30, 2005, Inventors: Juul-Mortensen et al. Sent Feb. 2, 2007.
Non-Final Office Action in U.S. Appl. No. 11/365,274, Filed Mar. 1, 2006, Inventors: Schlein et al. Sent Aug. 20, 2007.
Non-Final Office Action in U.S. Appl. No. 11/365,274, Filed Mar. 1, 2006, Inventors: Schlein et al. Sent Feb. 5, 2007.
Non-Final Office Action in U.S. Appl. No. 11/365,274, Filed Mar. 1, 2006, Inventors: Schlein et al. Sent Jan. 28, 2009.
Final Office Action in U.S. Appl. No. 10/185,923, Filed Jun. 27, 2002, Inventors: Funk et al. Sent Dec. 12, 2006.
Final Office Action in U.S. Appl. No. 10/185,923, Filed Jun. 27, 2002, Inventors: Funk et al. Sent Jun. 14, 2005.
Final Office Action in U.S. Appl. No. 10/185,923, Filed Jun. 27, 2002, Inventors: Hank et al. Sent Jun. 30, 2008.
Final Office Action in U.S. Appl. No. 11/290,635, Filed , Inventors: Juulmortensen et al. Sent Sep. 5, 2007.
Final Office Action in U.S. Appl. No. 11/290,635, Filed Nov. 30, 2005, Inventors: Juul-Mortensen et al. Sent Sep. 5, 2007.
Final Office Action in U.S. Appl. No. 11/365,274, Filed Mar. 1, 2006, Inventors: Schlein et al. Sent Apr. 4, 2008.
Final Office Action in U.S. Appl. No. 11/365,274, Filed Mar. 1, 2006, Inventors: Schlein et al. Sent Aug. 12, 2009.
Final Office Action in U.S. Appl. No. 11/786,095, Filed Apr. 11,2007, Inventors: Funk et al. Sent Nov. 24, 2009.
Final Office Action in U.S. Appl. No. 12/343,722, Filed Dec. 24, 2008, Inventors: Funk et al. Sent Feb. 18, 2009.
Brittain, Harry G., Buffers, Buffering Agents, and Ionic Equilibria, Encyclopedia of Pharmaceutical Technology, p. 385, 2007.
Remington's Pharmaceutical Sciences, Mack Publishing Company, 16th Edition, 1980, Chapter 79, p. 1406.
Plumer's Principles & Practice of Intravenous Therapy, 2006, Edition 8, pp. 124-128.
European Pharmacopoeia, 3rd Edition, 1997, pp. 17-18.
United States Pharmacopoeia, 24th Edition, 1999, pp. 1977-1978.
Further Experimental Data Jun. 22, 2009.
Frokjaer et al., Pharmaceutical Formulation Development of Peptides and Proteins, 2000, pp. 145-148 and 150-151.
Martin et al., Physical Pharmacy: Physical Chemical Principles in the Pharmaceutical Sciences, 1983, pp. 222-225.
Remington's Pharmaceutical Sciences, Mack Publishing Company, 18th Edition, 1990, Chapter 84, pp. 1545-1550.
Knudsen et al., J. Med. Chem., vol. 43, pp. 1664-1669, 2000.
Stenesh, J. Biochemistry, 1998, pp. 67-69.
Wang et al., J. Parenteral Science and Technology, vol. 42, pp. S4-S26, 1988.
Sigma Production Information on Gly Gly Buffer, Mar. 2010.
Martin et al., Physical Pharmacy, 1983, p. 232.
Declaration of Johnny C. Gonzalez, November 2010, pp. 1-7.
Eli Lilly and Company Product Information on Humalog Insulin Lispro Injection, 2009, pp. 1-12.
Eli Lilly & Co., Humalog Lispro Injection, USP Product Information Dated Feb. 11, 2010.

European Pharmacopoeia, 3rd Edition, 2.2.3, 1997, pp. 17-8, Council of Europe-Strasbourg.
Frokjaer & Hovgaard, Pharmaceutical Formulation Development of, 2000, pp. 145-148 & 150-151.
Further Experimental Data Dated Jun. 22, 2009.
Gonzales, Johnny C., Declaration of (Including Curriculum Vita) Dated Nov. 1, 2010 from Patent EP1412384.
Knudsen, L.B. et al., Potent Derivatives of Glucogon-Like Peptide-1, Journal of Medicinal Chemistry, 2000, vol. 43, pp. 1664-9.
Kristensen, H.G., Almen Farmaci, 2000, pp. 273-274, 281.
Mack Publishing Co., Remington's Pharmaceutical Sciences, 16th Edition, 1980, PT. 79, p. 1406.
Mack Publishing Co., Remington's Pharmaceutical Sciences, 18th Edition, 1990, Chapter 84, pp. 1545-50.
Martin A. et al., Physical Pharmacy; Physical Chemical Principles in the Pharmaceutical Sciences, 1983, 3rd Edition, p. 232.
Martin A. et al., Physical Pharmacy; Physical Chemical Principles in the Pharmaceutical Sciences, 1983, 3rd Edition, p. 323.
Sigma Product Information on Gly-Gly Buffer Dated Mar. 16, 2010.
Stenesh, J. Biochemistry, 1998, pp. 67-9.
United States Pharmacopoeia, 24th Edition, 1999, pp. 1977-8.
Villanueva Penacarril M.L. Potent Glycognic Effect of Glp-1(7-36) Amide in Rat Skeletal Muscle, Diabetologia, 1994, vol. 37, pp. 1163-6.
Wang & Hansen, Journal of Parenteral Science & Technology, 1988, vol. 42, pp. 4-26.
Weinstein, Sharon, Plumer's Principles & Practice of Intravenous, 2006, vol. 8 (8), pp. 124-8.
Duma et al., Pharmaceutical Dosage Forms: Parenteral Medications, vol. 1, 2nd Edition, p. 20.

* cited by examiner

Mannitol    Argi-    Inosi-    Glyce-

Myo-inositol　　　　　　　　Maltose　　　　　　　　　Glycerol

Glycine　　　　Lactose　　　　Mannitol

SEQUENCE LISTING

```
<160> NUMBER OF SEQ ID NOS: 1

<210> SEQ ID NO 1
<211> LENGTH: 44
<212> TYPE: PRT
<213> ORGANISM: artificial
<220> FEATURE:
<223> OTHER INFORMATION: synthetic
<220> FEATURE:
<221> NAME/KEY: MOD_RES
<222> LOCATION: (44)..(44)
<223> OTHER INFORMATION: Lysine at position 44 is amidated

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40
```

PROPYLENE GLYCOL-CONTAINING PEPTIDE FORMULATIONS WHICH ARE OPTIMAL FOR PRODUCTION AND FOR USE IN INJECTION DEVICES

CROSS REFERENCE TO RELATED APPLICATIONS

This Application is a continuation of International Application serial no. PCT/DK2004/000792 filed Nov. 18, 2004 and claims priority from U.S. application Ser. No. 60/524,653 filed Nov. 24, 2003 and from Danish Application serial no. PA 2003 01719 filed Nov. 20, 2003.

FIELD OF THE INVENTION

The present invention relates to pharmaceutical formulations comprising a peptide and propylene glycol, to methods of preparing such formulations, and to uses of such formulations in the treatment of diseases and conditions for which use of the peptide contained in such formulations is indicated. The present invention further relates to methods for reducing the clogging of injection devices by a peptide formulation and for reducing deposits on production equipment during production of a peptide formulation.

BACKGROUND OF THE INVENTION

The inclusion of isotonicity agents in peptide-containing pharmaceutical formulations is widely known and one of the more common isotonic agents used in such formulations is mannitol. However, the present inventors have observed that mannitol causes problems during the production of peptide formulations as it crystallizes resulting in deposits in the production equipment and in the final product. Such deposits increase the need to clean the filling equipment during production of the formulation and this results in reduced production capability. In addition, such deposits may also result in reduced yield of the final product since vials/cartridges containing the peptide formulation may need to be discarded if particles are present. Finally, the present inventors have observed that in peptide formulations to be administered by injection, the presence of mannitol results in clogging of injection devices.

Accordingly, it is desirable to identify an alternative isotonic agent to mannitol for inclusion in peptide-containing formulations and in particular, for inclusion in peptide formulations which are administered by injection.

SUMMARY OF THE INVENTION

The present inventors have discovered that peptide formulations containing propylene glycol at certain concentrations exhibit reduced deposits in production equipment and in the final product and also exhibit reduced clogging of injection devices. The present compositions may be formulated with any peptide and are also physically and chemically stable thus rendering them shelf-stable and suitable for invasive (e.g. injection, subcutaneous injection, intramuscular, intravenous or infusion) as well as non-invasive (e.g. nasal, oral, pulmonary, transdermal or transmucosal e.g. buccal) means of administration.

The present invention therefore relates to a pharmaceutical formulation comprising a peptide and propylene glycol, where the propylene glycol is present in a concentration of 1-100 mg/ml and the pH of the formulation is from 7-10. In a preferred embodiment, the pharmaceutical formulations of the invention further contain a buffer and a preservative.

The present invention also relates to methods for producing the pharmaceutical formulations of the invention.

In one embodiment, the method for preparing a peptide formulation comprises:
a) preparing a first solution by dissolving preservative, propylene glycol and buffer in water;
b) preparing a second solution by dissolving the peptide in water;
c) mixing the first and second solutions; and
d) adjusting the pH of the mixture in c) to the desired pH.

In another embodiment, the method for preparing a peptide formulation comprises:
a) preparing a first solution by dissolving preservative and buffer in water;
b) adding propylene glycol to the first solution;
c) mixing the first solution with a second solution containing peptide dissolved in water; and
d) adjusting the pH of the mixture in c) to the desired pH.

In yet another embodiment, the method for preparing a peptide formulation comprises:
a) preparing a solution by dissolving preservative, buffer and propylene glycol in water;
b) adding the peptide to the solution of step a); and
c) adjusting the pH of the solution of step b) to the desired pH.

The present invention further relates to methods of treatment using the pharmaceutical formulations of the invention where the compositions are administered in an amount effective to combat the disease, condition, or disorder for which administration of the peptide contained in the formulation is indicated.

In addition the present invention also relates to a method for reducing deposits on production equipment during production of a peptide formulation, where the method comprises replacing the isotonicity agent previously utilized in said formulation with propylene glycol at a concentration of between 1-100 mg/ml.

In one embodiment, the reduction in deposits on the production equipment during production by the propylene glycol-containing formulation relative to that observed for the formulation containing the previously utilized isotonicity agent is measured by a simulated filling experiment.

The present invention also relates to a method for reducing deposits in the final product during production of a peptide formulation, where the method comprises replacing the isotonicity agent previously utilized in said formulation with propylene glycol at a concentration of between 1-100 mg/ml.

In one embodiment, the reduction in deposits in the final product is measured by a reduction in the number of vials and/or cartridges of the propylene glycol-containing formulation that must be discarded due to deposits relative to number of vials and/or cartridges of the formulation containing the previously utilized isotonicity agent that must be discarded due to deposits.

The present invention further relates to a method for reducing the clogging of injection devices by a peptide formulation, where the method comprises replacing the isotonicity agent previously utilized in said formulation with propylene glycol at a concentration of between 1-100 mg/ml.

In one embodiment, the reduction in clogging of the injection device by the propylene glycol-containing formulation relative to that observed for the formulation containing the previously utilized isotonicity agent is measured in a simulated in use study.

DESCRIPTION OF THE INVENTION

Figure 1:
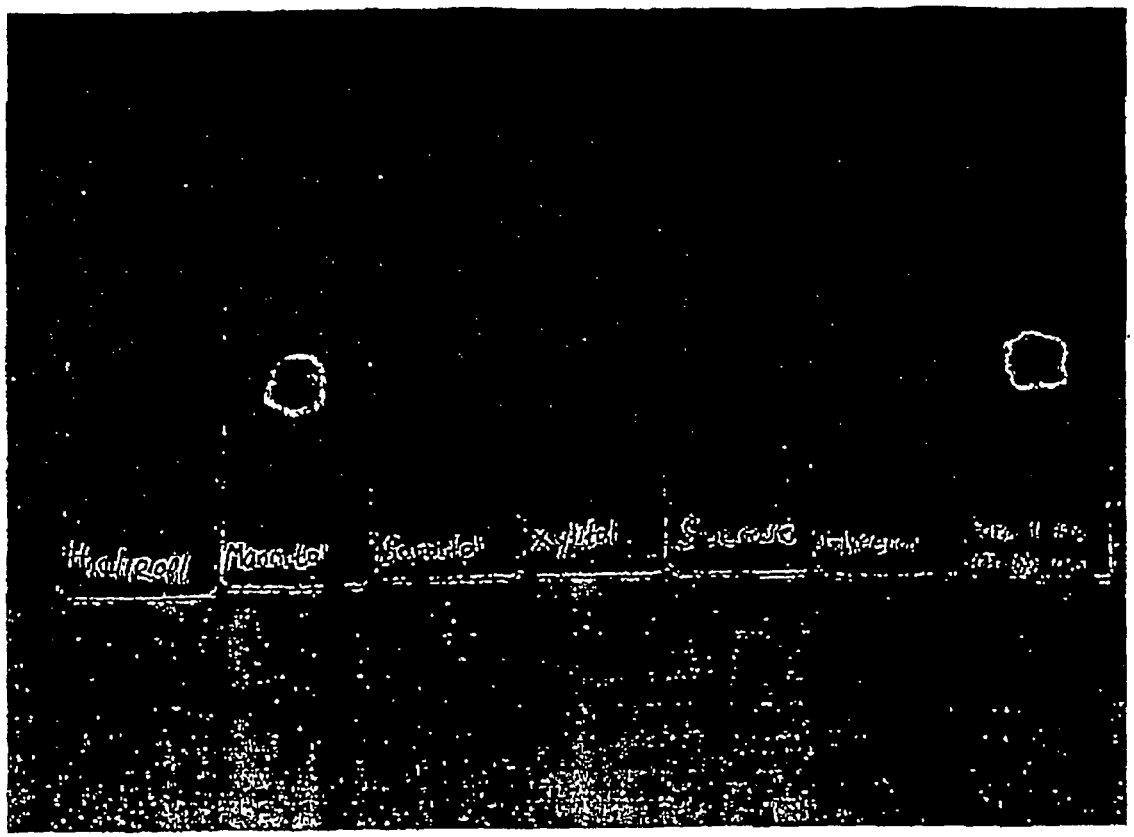
FIG. 1 shows a photograph of dried droplets on microscope slides of from left to right, placebo (no peptide) formulations containing no isotonic agent (e only water, preservative and buffer), mannitol, sorbitol, xylitol, sucrose or glycerol as the isotonic agent with the far right slide containing mannitol with peptide Arg$^{34}$, Lys$^{26}$(N$^{\epsilon}$-(γ-Glu(N$^{\alpha}$-hexadecanoyl)))-GLP-1(7-37).

The present invention relates to a pharmaceutical formulation comprising a peptide or a mixture of peptides and propylene glycol where the final concentration of propylene glycol in the formulation is 1-100 mg/ml and the pH of the formulation is in the range of from 7-10.

The pharmaceutical formulations of the invention are found to be optimal for production because they exhibit reduced deposits in production equipment relative to formulations containing other isotonicity agents as measured by the simulated filling studies described in the Examples. In addition, the pharmaceutical formulations of the invention are found to be optimal for use in injection devices because they exhibit reduced clogging of the injection devices relative to formulations containing other isotonicity agents as measured by the simulated in use studies described in the Examples.

The formulations of the present invention may be formulated with any peptide where examples of such peptides include, but are not limited to, glucagon, human growth hormone (hGH), insulin, aprotinin, FactorVII, tissue plasminogen activator (TPA), FactorVIIa, FFR-FactorVIIa, heparinase, ACTH, Heparin Binding Protein, corticotropin-releasing factor, angio-tensin, calcitonin, glucagon-like peptide-1, glucagon-like peptide-2, insulin-like growth factor-1, insulin-like growth factor-2, fibroblast growth factors, gastric inhibitory peptide, growth hormone-releasing factor, pituitary adenylate cyclase activating peptide, secretin, enterogastrin, somatostatin, somatomedin, parathyroid hormone, thrombopoietin, erythropoietin, hypothalamic releasing factors, prolactin, thyroid stimulating hormones, endorphins, enkephalins, vasopressin, oxytocin, opiods, DPP IV, interleukins, immunoglobulins, complement inhibitors, serine protease inhibitors, cytokines, cytokine receptors, PDGF, tumor necrosis factors, tumor necrosis factors receptors, growth factors and analogues as well as derivatives thereof where each of these peptides constitutes an alternative embodiment of the present invention.

In the present application, the designation "an analogue" is used to designate a peptide wherein one or more amino acid residues of the parent peptide have been substituted by another amino acid residue and/or wherein one or more amino acid residues of the parent peptide have been deleted and/or wherein one or more amino acid residues have been added to the parent peptide. Such addition can take place either at the N-terminal end or at the C-terminal end of the parent peptide or both. Typically "an analogue" is a peptide wherein 6 or less amino acids have been substituted and/or added and/or deleted from the parent peptide, more preferably a peptide wherein 3 or less amino acids have been substituted and/or added and/or deleted from the parent peptide, and most preferably, a peptide wherein one amino acid has been substituted and/or added and/or deleted from the parent peptide.

In the present application, "a derivative" is used to designate a peptide or analogue thereof which is chemically modified by introducing an organic substituent e.g. ester, alkyl or lipophilic functionalities, on one or more amino acid residues of the peptide or analogue thereof.

In one embodiment, the peptide to be included in the formulation of the invention is a GLP-1 agonist where "a GLP-1 agonist" is understood to refer to any peptide which fully or partially activates the human GLP-1 receptor. In a preferred embodiment, the "GLP-1 agonist" is any peptide that binds to a GLP-1 receptor, preferably with an affinity constant ($K_D$) or a potency ($EC_{50}$) of below 1 μM, e.g. below 100 nM as measured by methods known in the art (see e.g. WO 98/08871) and exhibits insulinotropic activity, where insulinotropic activity may be measured in vivo or in vitro assays known to those of ordinary skill in the art. For example, the GLP-1 agonist may be administered to an animal and the insulin concentration measured over time.

Methods for identifying GLP-1 agonists are described in WO 93/19175 (Novo Nordisk A/S) and examples of suitable GLP-1 analogues and derivatives which can be used according to the present invention includes those referred to in WO 99/43705 (Novo Nordisk A/S), WO 99/43706 (Novo Nordisk A/S), WO 99/43707 (Novo Nordisk A/S), WO 98/08871 (analogues with lipophilic substituent) and in WO 02/46227 (analogues fused to serum albumin or to Fc portion of an Ig).(Novo Nordisk A/S), WO 99/43708 (Novo Nordisk A/S), WO 99/43341 (Novo Nordisk A/S), WO 87/06941 (The General Hospital Corporation), WO 90/11296 (The General Hospital Corporation), WO 91/11457 (Buckley et al.), WO 98/43658 (Eli Lilly & Co.), EP 0708179-A2 (Eli Lilly & Co.), EP 0699686-A2 (Eli Lilly & Co.), WO 01/98331 (Eli Lilly & Co).

In one embodiment, the GLP-1 agonist is selected from the group consisting of GLP-1(7-36)-amide, GLP-1(7-37), a GLP-1(7-36)-amide analogue, a GLP-1(7-37) analogue, or a derivative of any of these.

In one embodiment, the GLP-1 agonist is a derivative of GLP-1(7-36)-amide, GLP-1(7-37), a GLP-1(7-36)-amide analogue or a GLP-1(7-37) analogue, which comprises a lipophilic substituent.

In this embodiment of the invention, the GLP-1 derivative preferably has three lipophilic substituents, more preferably two lipophilic substituents, and most preferably one lipophilic substituent attached to the parent peptide (ie GLP-1(7-36)-amide, GLP-1(7-37), a GLP-1(7-36)-amide analogue or a GLP-1(7-37) analogue), where each lipophilic substituent(s) preferably has 4-40 carbon atoms, more preferably 8-30 carbon atoms, even more preferably 8-25 carbon atoms, even more preferably 12-25 carbon atoms, and most preferably 14-18 carbon atoms.

In one embodiment, the lipophilic substituent comprises a partially or completely hydrogenated cyclopentanophenathrene skeleton.

In another embodiment, the lipophilic substituent is a straight-chain or branched alkyl group.

In yet another embodiment, the lipophilic substituent is an acyl group of a straight-chain or branched fatty acid. Preferably, the lipophilic substituent is an acyl group having the formula $CH_3(CH_2)_nCO-$, wherein n is an integer from 4 to 38, preferably an integer from 12 to 38, and most preferably is $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$ and $CH_3(CH_2)_{22}CO-$. In a more preferred embodiment, the lipophilic substituent is tetradecanoyl. In a most preferred embodiment, the lipophilic substituent is hexadecanoyl.

In a further embodiment of the present invention, the lipophilic substituent has a group which is negatively charged such as a carboxylic acid group. For example, the lipophilic substituent may be an acyl group of a straight-chain or branched alkane α,ω-dicarboxylic acid of the formula $HOOC(CH_2)_mCO-$, wherein m is an integer from 4 to 38, preferably an integer from 12 to 38, and most preferably is $HOOC(CH_2)_{14}CO-$, $HOOC(CH_2)_{16}CO-$, $HOOC(CH_2)_{18}CO-$, $HOOC(CH_2)_{20}CO-$ or $HOOC(CH_2)_{22}CO-$.

In the GLP-1 derivatives of the invention, the lipophilic substituent(s) contain a functional group which can be attached to one of the following functional groups of an amino acid of the parent GLP-1 peptide:

(a) the amino group attached to the alpha-carbon of the N-terminal amino acid,
(b) the carboxy group attached to the alpha-carbon of the C-terminal amino acid,
(c) the epsilon-amino group of any Lys residue,
(d) the carboxy group of the R group of any Asp and Glu residue,
(e) the hydroxy group of the R group of any Tyr, Ser and Thr residue,
(f) the amino group of the R group of any Trp, Asn, Gln, Arg, and His residue, or
(g) the thiol group of the R group of any Cys residue.

In one embodiment, a lipophilic substituent is attached to the carboxy group of the R group of any Asp and Glu residue.

In another embodiment, a lipophilic substituent is attached to the carboxy group attached to the alpha-carbon of the C-terminal amino acid.

In a most preferred embodiment, a lipophilic substituent is attached to the epsilon-amino group of any Lys residue.

In a preferred embodiment of the invention, the lipophilic substituent is attached to the parent GLP-1 peptide by means of a spacer. A spacer must contain at least two functional groups, one to attach to a functional group of the lipophilic substituent and the other to a functional group of the parent GLP-1 peptide.

In one embodiment, the spacer is an amino acid residue except Cys or Met, or a dipeptide such as Gly-Lys. For purposes of the present invention, the phrase "a dipeptide such as Gly-Lys" means any combination of two amino acids except Cys or Met, preferably a dipeptide wherein the C-terminal amino acid residue is Lys, His or Trp, preferably Lys, and the N-terminal amino acid residue is Ala, Arg, Asp, Asn, Gly, Glu, Gln, Ile, Leu, Val, Phe, Pro, Ser, Tyr, Thr, Lys, His and Trp. Preferably, an amino group of the parent peptide forms an amide bond with a carboxylic group of the amino acid residue or dipeptide spacer, and an amino group of the amino acid residue or dipeptide spacer forms an amide bond with a carboxyl group of the lipophilic substituent.

Preferred spacers are lysyl, glutamyl, asparagyl, glycyl, beta-alanyl and gamma-aminobutanoyl, each of which constitutes an individual embodiment. Most preferred spacers are glutamyl and beta-alanyl. When the spacer is Lys, Glu or Asp, the carboxyl group thereof may form an amide bond with an amino group of the amino acid residue, and the amino group thereof may form an amide bond with a carboxyl group of the lipophilic substituent. When Lys is used as the spacer, a further spacer may in some instances be inserted between the ε-amino group of Lys and the lipophilic substituent. In one embodiment, such a further spacer is succinic acid which forms an amide bond with the ε-amino group of Lys and with an amino group present in the lipophilic substituent. In another embodiment such a further spacer is Glu or Asp which forms an amide bond with the ε-amino group of Lys and another amide bond with a carboxyl group present in the lipophilic substituent, that is, the lipophilic substituent is a $N^\epsilon$-acylated lysine residue.

In another embodiment, the spacer is an unbranched alkane α,ω-dicarboxylic acid group having from 1 to 7 methylene groups, which spacer forms a bridge between an amino group of the parent peptide and an amino group of the lipophilic substituent. Preferably, the spacer is succinic acid.

In a further embodiment, the lipophilic substituent with the attached spacer is a group of the formula $CH_3(CH_2)_pNH-CO(CH_2)_qCO-$, wherein p is an integer from 8 to 33, preferably from 12 to 28 and q is an integer from 1 to 6, preferably 2.

In a further embodiment, the lipophilic substituent with the attached spacer is a group of the formula $CH_3(CH_2)_rCO-NHCH(COOH)(CH_2)_2CO-$, wherein r is an integer from 4 to 24, preferably from 10 to 24.

In a further embodiment, the lipophilic substituent with the attached spacer is a group of the formula $CH_3(CH_2)_sCO-NHCH((CH_2)_2COOH)CO-$, wherein s is an integer from 4 to 24, preferably from 10 to 24.

In a further embodiment, the lipophilic substituent is a group of the formula $COOH(CH_2)_tCO-$ wherein t is an integer from 6 to 24.

In a further embodiment, the lipophilic substituent with the attached spacer is a group of the formula $-NHCH(COOH)(CH_2)_4NH-CO(CH_2)_uCH_3$, wherein u is an integer from 8 to 18.

In a further embodiment, the lipophilic substituent with the attached spacer is a group of the formula $CH_3(CH_2)_vCO-NH-(CH_2)_z-CO$, wherein v is an integer from 4 to 24 and z is an integer from 1 to 6.

In a further embodiment, the lipophilic substituent with the attached spacer is a group of the formula $-NHCH(COOH)(CH_2)_4NH-COCH((CH_2)_2COOH)NH-CO(CH_2)_wCH_3$, wherein w is an integer from 10 to 16.

In a further embodiment, the lipophilic substituent with the attached spacer is a group of the formula $-NHCH(COOH)(CH_2)_4NH-CO(CH_2)_2CH(COOH)NHCO(CH_2)_xCH_3$, wherein x is zero or an integer from 1 to 22, preferably 10 to 16.

In yet another embodiment the GLP-1 agonist is $Arg^{34}$, $Lys^{26}(N^\epsilon-(\gamma-Glu(N^\alpha-hexade-canoyl)))-GLP-1(7-37)$.

In yet another embodiment the GLP-1 agonist is selected from the group consisting of $Gly^8$-GLP-1(7-36)-amide, $Gly^8$-GLP-1(7-37), $Val^8$-GLP-1(7-36)-amide, $Val^8$-GLP-1(7-37), $Val^8Asp^{22}$-GLP-1(7-36)-amide, $Val^8Asp^{22}$-GLP-1(7-37), $Val^8Glu^{22}$-GLP-1(7-36)-amide, $Val^8Glu^{22}$-GLP-1(7-37), $Val^8Lys^{22}$-GLP-1(7-36)-amide, $Val^8Lys^{22}$-GLP-1(7-37), $Val^8Arg^{22}$-GLP-1(7-36)-amide, $Val^8Arg^{22}$-GLP-1(7-37), Val$^8$His$^{22}$-GLP-1(7-36)-amide, Val$^8$His$^{22}$-GLP-1(7-37), analogues thereof and derivatives of any of these.

In yet another embodiment the GLP-1 agonist is selected from the group consisting of Arg$^{26}$-GLP-1(7-37); Arg$^{34}$-GLP-1(7-37); Lys$^{36}$-GLP-1(7-37); Arg$^{26,34}$Lys$^{36}$-GLP-1(7-37); Arg$^{26,34}$-GLP-1(7-37); Arg$^{26,34}$Lys$^{40}$-GLP-1(7-37); Arg$^{26}$Lys$^{36}$-GLP-1(7-37); Arg$^{34}$Lys$^{36}$-GLP-1(7-37); Val$^8$Arg$^{22}$-GLP-1(7-37); Met$^8$Arg$^{22}$-GLP-1(7-37); Gly$^8$His$^{22}$-GLP-1(7-37); Val$^8$His$^{22}$-GLP-1(7-37); Met$^8$His$^{22}$-GLP-1(7-37); His$^{37}$-GLP-1(7-37); Gly$^8$-GLP-1(7-37); Val$^8$-GLP-1(7-37); Met$^8$-GLP-1(7-37); Gly$^8$Asp$^{22}$-GLP-1(7-37); Val$^8$Asp$^{22}$-GLP-1(7-37); Met$^8$Asp$^{22}$-GLP-1(7-37); Gly$^8$Glu$^{22}$-GLP-1(7-37); Val$^8$Glu$^{22}$-GLP-1(7-37); Met$^8$Glu$^{22}$-GLP-1(7-37); Gly$^8$Lys$^{22}$-GLP-1(7-37); Val$^8$Lys$^{22}$-GLP-1(7-37); Met$^8$Lys$^{22}$-GLP-1(7-37); Gly$^8$Arg$^{22}$-GLP-1(7-37); Val$^8$Lys$^{22}$His$^{37}$-GLP-1(7-37); Gly$^8$Glu$^{22}$His$^{37}$-GLP-1(7-37); Val$^8$Glu$^{22}$His$^{37}$-GLP-1(7-37); Met$^8$Glu$^{22}$His$^{37}$-GLP-1(7-37); Gly$^8$Lys$^{22}$ His$^{37}$-GLP-1(7-37); Met$^8$Lys$^{22}$His$^{37}$-GLP-1(7-37); Gly$^8$Arg$^{22}$His$^{37}$-GLP-1(7-37); Val$^8$Arg$^{22}$His$^{37}$-GLP-1(7-37); Met$^8$Arg$^{22}$His$^{37}$-GLP-1(7-37); Gly$^8$His$^{22}$His$^{37}$-GLP-1(7-37); Val$^8$His$^{22}$His$^{37}$-GLP-1(7-37); Met$^8$His$^{22}$His $^{37}$-GLP-1(7-37); Gly$^8$His$^{37}$-GLP-1(7-37); Val$^8$His$^{37}$-GLP-1(7-37); Met$^8$His$^{37}$-GLP-1(7-37); Gly$^8$Asp$^{22}$His$^{37}$-GLP-1(7-37); Val$^8$Asp$^{22}$His$^{37}$-GLP-1(7-37); Met$^8$Asp$^{22}$His$^{37}$-GLP-1(7-37); Arg$^{26}$-GLP-1(7-36)-amide; Arg$^{34}$-GLP-1(7-36)-amide; Lys$^{36}$-GLP-1(7-36)-amide; Arg$^{26,34}$Lys$^{36}$-GLP-1(7-36)-amide; Arg$^{26,34}$-GLP-1(7-36)-amide; Arg$^{26,34}$Lys$^{40}$-GLP-1(7-36)-amide; Arg$^{26}$Lys$^{36}$-GLP-1(7-36)-amide; Arg$^{34}$Lys$^{36}$-GLP-1(7-36)-amide; Gly$^8$-GLP-1(7-36)-amide; Val$^8$-GLP-1(7-36)-amide; Met$^8$-GLP-1(7-36)-amide; Gly$^8$Asp$^{22}$-GLP-1(7-36)-amide; Gly$^8$Glu$^{22}$His$^{37}$-GLP-1(7-36)-amide; Val$^8$Asp$^{22}$-GLP-1(7-36)-amide; Met$^8$Asp$^{22}$-GLP-1(7-36)-amide; Gly$^8$Glu$^{22}$-GLP-1(7-36)-amide; Val$^8$Glu$^{22}$-GLP-1(7-36)-amide; Met$^8$Glu$^{22}$-GLP-1(7-36)-amide; Gly$^8$Lys$^{22}$-GLP-1(7-36)-amide; Val$^8$Lys$^{22}$-GLP-1(7-36)-amide; Met$^8$Lys$^{22}$-GLP-1(7-36)-amide; Gly$^8$His$^{22}$His$^{37}$-GLP-1(7-36)-amide; Gly$^8$Arg$^{22}$-GLP-1(7-36)-amide; Val$^8$Arg$^{22}$-GLP-1(7-36)-amide; Met$^8$Arg$^{22}$-GLP-1(7-36)-amide; Gly$^8$His$^{22}$-GLP-1(7-36)-amide; Val$^8$His$^{22}$-GLP-1(7-36)-amide; Met$^8$His$^{22}$-GLP-1(7-36)-amide; His$^{37}$-GLP-1(7-36)-amide; Val$^8$Arg$^{22}$His$^{37}$-GLP-1(7-36)-amide; Met$^8$Arg$^{37}$-GLP-1(7-36)-amide; Gly$^8$His$^{37}$-GLP-1(7-36)-amide; Val$^8$His$^{37}$-GLP-1(7-36)-amide; Met$^8$His$^{37}$-GLP-1(7-36)-amide; Gly$^8$Asp$^{22}$ His$^{37}$-GLP-1(7-36)-amide; Val$^8$Asp$^{22}$His$^{37}$-GLP-1(7-36)-amide; Met$^8$Asp$^{22}$His$^{37}$-GLP-1(7-36)-amide; Val$^8$Glu$^{22}$His$^{37}$-GLP-1(7-36)-amide; Met$^8$Glu$^{22}$His$^{37}$-GLP-1(7-36)-amide; Gly$^8$Lys$^{22}$His$^{37}$-GLP-1(7-36)-amide; Val$^8$Lys$^{22}$His$^{37}$-GLP-1(7-36)-amide; Met$^8$Lys$^{22}$His$^{37}$-GLP-1(7-36)-amide; Gly$^8$Arg$^{22}$His$^{37}$-GLP-1(7-36)-amide; Val$^8$His$^{22}$His$^{37}$-GLP-1(7-36)-amide; Met$^8$His$^{22}$His$^{37}$-GLP-1(7-36)-amide; and derivatives thereof.

In yet another embodiment the GLP-1 agonist is selected from the group consisting of Val$^8$Trp$^{19}$Glu$^{22}$-GLP-1(7-37), Val$^8$Glu$^{22}$Val$^{25}$-GLP-1(7-37), Val$^8$Tyr$^{16}$Glu$^{22}$-GLP-1(7-37), Val$^8$Trp$^{16}$Glu$^{22}$-GLP-1(7-37), Val$^8$Leu$^{16}$Glu$^{22}$-GLP-1(7-37), Val$^8$Tyr$^{18}$Glu$^{22}$-GLP-1(7-37), Val$^8$Glu$^{22}$ His$^{37}$-GLP-1(7-37), Val$^8$Glu$^{22}$Ile$^{33}$-GLP-1(7-37), Val$^8$Trp$^{16}$Glu$^{22}$Val$^{25}$Ile$^{33}$-GLP-1(7-37), Val$^8$Trp$^{16}$Glu$^{22}$Ile$^{33}$-GLP-1(7-37), Val$^8$Glu$^{22}$Val$^{25}$Ile$^{33}$-GLP-1(7-37), Val$^8$Trp$^{16}$Glu$^{22}$Val$^{25}$-GLP-1(7-37), analogues thereof and derivatives of any of these.

In yet another embodiment the GLP-1 agonist is exendin-4 or exendin-3, an exendin-4 or exendin-3 analogue or a derivative of any of these.

Examples of exendins as well as analogues, derivatives, and fragments thereof to be included within the present invention are those disclosed in WO 97/46584, U.S. Pat. No. 5,424,286 and WO 01/04156. U.S. Pat. No. 5,424,286 describes a method for stimulating insulin release with an exendin polypeptide. The exendin polypeptides disclosed include HGEGTFTSDLSKQMEEEAVRLFIEWLKNGGX; wherein X=P or Y, and HX1X2GTFITSDLSKQMEEEAVRLFIEWLKNGGPSSGAPPPS; wherein X1X2=SD (exendin-3) or GE (exendin-4)). WO 97/46584 describes truncated versions of exendin peptide(s). The disclosed peptides increase secretion and biosynthesis of insulin, but reduce those of glucagon. WO 01/04156 describes exendin-4 analogues and derivatives as well as the preparation of these molecules. Exendin-4 analogues stabilized by fusion to serum albumin or Fc portion of an Ig are disclosed in WO 02/46227.

In one embodiment, the exendin-4 analogue is HGEGTFTSDLSKQMEEEAVRLFIEWLKNGGPSS-GAPPSKKKKKK-amide.

Where the peptide to be included in the formulation of the invention is a GLP-1 agonist, the GLP-1 agonist is present in a concentration from about 0.1 mg/ml to about 100 mg/ml, more preferably in a concentration from about 0.1 mg/ml to about 50 mg/ml, and most preferably in a concentration of from about 0.1 mg/ml to about 10 mg/ml.

In another embodiment, the peptide to be included in the formulation of the invention is insulin, where "insulin" is understood to mean human insulin, [where "human insulin" means insulin having the amino acid sequence shown in DSHW Nicol and L F Smith: *Nature,* (1960) 4736:483-485, which is hereby incorporated by reference], human insulin analogs, human insulin derivatives or mixtures thereof, where examples of insulin analogs and derivatives are those disclosed in EP 0 792 290 (Novo Nordisk A/S), EP 0 214 826 and EP 0 705 275 (Novo Nordisk A/S), U.S. Pat. No. 5,504,188 (Eli Lilly), EP 0 368 187 (Aventis), U.S. Pat. Nos. 5,750,497 and 6,011,007, EP 375437 and EP 383472 and where such insulins may include, but are not limited to, NPH insulin, Lys β29 (Nε-tetradecanoyl) des(B30) human insulin, Lys$^{B29}$-(N$^\epsilon$-(γ-glutamyl-N$^\alpha$-lithocholyl) des(B30) human insulin, N$^{LB29}$-octanoyl insulin, 30/70 mixtures of prompt insulin zinc (SEMILENTE®) with extended insulin zinc (ULTRALENTE®), sold commercially as LENTE®, insulin glargine (LANTUS®) or extended insulin zinc (ULTRALENTE®), Lys$^{B28}$ Pro$^{B29}$ human insulin (HUMALOG®), Asp$^{B28}$ human insulin, insulin aspart (NOVOLOG®), or a 30/70 mixture of insulin aspart and insulin aspart protamine (NOVOMIX®).

In one embodiment, the insulin is a derivative of human insulin or a human insulin analogue where the derivative contains at least one lysine residue and a lipophilic substituent is attached to the epsilon amino group of the lysine residue.

In one embodiment, the lysine residue to which the lipophilic substituent is attached is present at position B28 of the insulin peptide.

In an alternative embodiment, the lysine residue to which the lipophilic substituent is attached is present at position B29 of the insulin peptide.

In yet another embodiment, lipophilic substituent is an acyl group corresponding to a carboxylic acid having at least 6 carbon atoms.

In another preferred embodiment, the lipophilic substituent is an acyl group, branched or unbranched, which corresponds to a carboxylic acid having a chain of carbon atoms 8 to 24 atoms long.

In another preferred embodiment, the lipophilic substituent is an acyl group corresponding to a fatty acid having at least 6 carbon atoms.

In another preferred embodiment, the lipophilic substituent is an acyl group corresponding to a linear, saturated carboxylic acid having from 6 to 24 carbon atoms.

In another preferred embodiment, the lipophilic substituent is an acyl group corresponding to a linear, saturated carboxylic acid having from 8 to 12 carbon atoms.

In another preferred embodiment, the lipophilic substituent is an acyl group corresponding to a linear, saturated carboxylic acid having from 10 to 16 carbon atoms.

In another preferred embodiment, the lipophilic substituent is an oligo oxyethylene group comprising up to 10, preferably up to 5, oxyethylene units.

In another preferred embodiment, the lipophilic substituent is an oligo oxypropylene group comprising up to 10, preferably up to 5, oxypropylene units.

In one preferred embodiment, the invention relates to a human insulin derivative in which the B30 amino acid residue is deleted or is any amino acid residue which can be coded for by the genetic code except Lys, Arg and Cys; the A21 and the B3 amino acid residues are, independently, any amino acid residues which can be coded for by the genetic code except Lys, Arg and Cys; $Phe^{B1}$ may be deleted; the $\square$-amino group of $Lys^{B29}$ has a lipophilic substituent which comprises at least 6 carbon atoms; and 2-4 $Zn^{2+}$ ions may be bound to each insulin hexamer with the proviso that when B30 is Thr or Ala and A21 and B3 are both Asn, and $Phe^{B1}$ is not deleted, then 2-4 $Zn^{2+}$ ions are bound to each hexamer of the insulin derivative.

In another preferred embodiment, the invention relates to a human insulin derivative in which the B30 amino acid residue is deleted or is any amino acid residue which can be coded for by the genetic code except Lys, Arg and Cys; the A21 and the B3 amino acid residues are, independently, any amino acid residues which can be coded for by the genetic code except Lys, Arg and Cys, with the proviso that if the B30 amino acid residue is Ala or Thr, then at least one of the residues A21 and B3 is different from Asn; $Phe^{B1}$ may be deleted; and the $\square$-amino group of $Lys^{B29}$ has a lipophilic substituent which comprises at least 6 carbon atoms.

In another preferred embodiment, the invention relates to a human insulin derivative in which the B30 amino acid residue is deleted or is any amino acid residue which can be coded for by the genetic code except Lys, Arg and Cys; the A21 and the B3 amino acid residues are, independently, any amino acid residues which can be coded for by the genetic code except Lys, Arg and Cys; $Phe^{B1}$ may be deleted; the $\square$-amino group of $Lys^{B29}$ has a lipophilic substituent which comprises at least 6 carbon atoms; and 2-4 $Zn^{2+}$ ions are bound to each insulin hexamer.

Where the peptide to be included in the formulation of the invention is an insulin, the insulin is present in a concentration from about 0.5 mg/ml to about 20 mg/ml, more preferably in a concentration from about 1 mg/ml to about 15 mg/ml.

In another embodiment, the peptide to be included in the formulations of the invention is hGH or Met-hGH.

Where the peptide to be included in the formulation of the invention is hGH or Met-hGH, the hGH or Met-hGH is present in a concentration from about 0.5 mg/ml to about 50 mg/ml, more preferably in a concentration from about 1 mg/ml to about 10 mg/ml.

In yet another embodiment, the peptide to be included in the formulations of the invention is GLP-2 or an analogue or derivative thereof.

Where the peptide to be included in the formulation of the invention is GLP-2 or an analogue or derivative thereof, the GLP-2 or an analogue or derivative thereof is present in a concentration from about 1 mg/ml to about 100 mg/ml, more preferably in a concentration from about 1 mg/ml to about 10 mg/ml.

In yet a further embodiment, the peptide to be included in the formulations of the invention is Factor VII or Factor VIIa or an analogue or derivative thereof.

Where the peptide to be included in the formulation of the invention is Factor VII or Factor VIIa or an analogue or derivative thereof, the Factor VII or Factor VIIa or an analogue or derivative thereof is present in a concentration from about 0.1 mg/ml to about 10 mg/ml, more preferably in a concentration from about 0.5 mg/ml to about 5 mg/ml.

In one embodiment, the final concentration of propylene glycol in the formulations of the invention is from about 1 to about 50 mg/ml.

In another embodiment, the final concentration of propylene glycol in the formulations of the invention is from about 5 to about 25 mg/ml.

In yet another embodiment, the final concentration of propylene glycol in the formulations of the invention is from about 8 to about 16 mg/ml.

In yet a further embodiment, the final concentration of propylene glycol in the formulations of the invention is from about 13 to about 15 mg/ml.

In still another embodiment, the final concentration of propylene glycol in the formulations of the invention is from about 13.5 to about 14.5 mg/ml.

In another embodiment of the invention, the formulation has a pH in the range from about 7.0 to about 9.5 where the term "about" as used in connection with pH means + or −0.1 pH units from the stated number.

In a further embodiment of the invention, the formulation has a pH in the range from about 7.0 to about 8.0.

In yet a further embodiment of the invention, the formulation has a pH in the range from about 7.2 to about 8.0.

In a further embodiment of the invention, the formulation has a pH in the range from about 7.0 to about 8.3.

In yet a further embodiment of the invention, the formulation has a pH in the range from about 7.3 to about 8.3.

In a preferred embodiment of the invention, the formulations contain, in addition to a peptide and propylene glycol, a buffer and/or a preservative.

Where a buffer is to be included in the formulations of the invention, the buffer is selected from the group consisting of sodium acetate, sodium carbonate, citrate, glycylglycine, histidine, glycine, lysine, arginin, sodium dihydrogen phosphate, disodium hydrogen phosphate, sodium phosphate, and tris(hydroxymethyl)-aminomethan, or mixtures thereof. Each one of these specific buffers constitutes an alternative embodiment of the invention. In a preferred embodiment of the invention the buffer is glycylglycine, sodium dihydrogen phosphate, disodium hydrogen phosphate, sodium phosphate or mixtures thereof.

Where a pharmaceutically acceptable preservative is to be included in the formulations of the invention, the preservative is selected from the group consisting of phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. Each one of these specific preservatives constitutes an alternative embodiment of the invention. In a preferred embodiment of the invention the preservative is phenol or m-cresol.

In a further embodiment of the invention the preservative is present in a concentration from about 0.1 mg/ml to about 50 mg/ml, more preferably in a concentration from about 0.1 mg/ml to about 25 mg/ml, and most preferably in a concentration from about 0.1 mg/ml to about 10 mg/ml The use of a preservative in pharmaceutical compositions is well-known to the skilled person. For convenience reference is made to Remington: *The Science and Practice of Pharmacy*, 19$^{th}$ edition, 1995.

In a further embodiment of the invention the formulation may further comprise a chelating agent where the chelating agent may be selected from salts of ethlenediaminetetraacetic acid (EDTA), citric acid, and aspartic acid, and mixtures thereof. Each one of these specific chelating agents constitutes an alternative embodiment of the invention.

In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml.

The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation may further comprise a stabilizer selected from the group of high molecular weight polymers or low molecular compounds where such stabilizers include, but are not limited to, polyethylene glycol (e.g. PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, threonine and mixtures thereof. Each one of these specific stabilizers constitutes an alternative embodiment of the invention. In a preferred embodiment of the invention the stabilizer is selected from the group consisting of L-histidine, imidazole and arginine.

In a further embodiment of the invention the high molecular weight polymer is present in a concentration from 0.1 mg/ml to 50 mg/ml. In a further embodiment of the invention the high molecular weight polymer is present in a concentration from 0.1 mg/ml to 5 mg/ml. In a further embodiment of the invention the high molecular weight polymer is present in a concentration from 5 mg/ml to 10 mg/ml. In a further embodiment of the invention the high molecular weight polymer is present in a concentration from 0 mg/ml to 20 mg/ml. In a further embodiment of the invention the high molecular weight polymer is present in a concentration from 20 mg/ml to 30 mg/ml. In a further embodiment of the invention the high molecular weight polymer is present in a concentration from 30 mg/ml to 50 mg/ml.

In a further embodiment of the invention the low molecular weight compound is present in a concentration from 0.1 mg/ml to 50 mg/ml. In a further embodiment of the invention the low molecular weight compound is present in a concentration from 0.1 mg/ml to 5 mg/ml. In a further embodiment of the invention the low molecular weight compound is present in a concentration from 5 mg/ml to 10 mg/ml. In a further embodiment of the invention the low molecular weight compound is present in a concentration from 10 mg/ml to 20 mg/ml. In a further embodiment of the invention the low molecular weight compound is present in a concentration from 20 mg/ml to 30 mg/ml. In a further embodiment of the invention the low molecular weight compound is present in a concentration from 30 mg/ml to 50 mg/ml.

The use of a stabilizer in pharmaceutical compositions is well-known to the skilled person. For convenience reference is made to Remington: *The Science and Practice of Pharmacy*, 19$^{th}$ edition, 1995.

In a further embodiment of the invention the formulation of the invention may further comprise a surfactant where a surfactant may be selected from a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g. Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, docusate calcium, docusate potassium, SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propane-sulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the postively charged DODAC, DOTMA, DCP, BISHOP, lysophosphatidylserine and lysophosphatidylthreonine, zwitterionic surfactants (e.g. N-alkyl-N,N-dimethylammonio-1-propanesulfonates, 3-cholamido-1-propyldimethylammonio-1-propane-sulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives—(e.g. sodium tauro-dihydrofusidate etc.), long-chain fatty acids and salts thereof C6-C12 (e.g. oleic acid and caprylic acid), acylcarnitines and derivatives, N$^\alpha$-acylated derivatives of lysine, arginine or histidine, or side-chain acylated derivatives of lysine or arginine, N$^\alpha$-acylated derivatives of dipeptides comprising any combination of lysine, arginine or histidine and a neutral or acidic amino acid, N$^\alpha$-acylated derivative of a tripeptide comprising any combination of a neutral amino acid and two charged amino acids, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 19$^{th}$ edition, 1995.

The formulations of the invention may be prepared by conventional techniques, e.g. as described in Remington's *Pharmaceutical Sciences*, 1985 or in Remington: *The Science and Practice of Pharmacy*, 19$^{th}$ edition, 1995, where such conventional techniques of the pharmaceutical industry involve dissolving and mixing the ingredients as appropriate to give the desired end product.

As mentioned above, in a preferred embodiment, the formulations of the invention-contain, in addition to a peptide and propylene glycol, a buffer and/or a preservative.

In one embodiment, the method for preparing such a peptide formulation comprises:
a) preparing a first solution by dissolving preservative, propylene glycol and buffer in water;
b) preparing a second solution by dissolving the peptide in water;
c) mixing the first and second solutions; and
d) adjusting the pH of the mixture in c) to the desired pH.

In another embodiment, the method for preparing such a peptide formulation comprises:
a) preparing a first solution by dissolving preservative and buffer in water;
b) adding propylene glycol to the first solution;
c) mixing the first solution with a second solution containing peptide dissolved in water; and
d) adjusting the pH of the mixture in c) to the desired pH.

In yet another embodiment, the method for preparing a peptide formulation comprises:
a) preparing a solution by dissolving preservative, buffer and propylene glycol in water;
b) adding the peptide to the solution of step a); and
c) adjusting the pH of the solution of step b) to the desired pH.

As the formulations of the invention are optimal for production and for use in injection devices since they exhibit reduced deposits of production equipment and reduced clogging of injection devices, the above methods of production can be used to produce peptide formulations suitable for use in production and/or for use in injection devices.

The formulations of the invention are suitable for administration to a mammal, preferably a human. The route of administration of the formulations of the invention may be any route which effectively transports the peptide contained in the formulation to the appropriate or desired site of action, such as oral, nasal, buccal, pulmonal, transdermal or parenteral.

Due to the ability of propylene glycol to reduce clogging of injection devices when compared to other isotonic agents and to mannitol in particular, in a preferred embodiment, the formulations of the invention are to be administered parenterally to a patient in need thereof. Parenteral administration may be performed by subcutaneous, intramuscular or intravenous injection by means of a syringe, optionally a pen-like syringe. Alternatively, parenteral administration can be performed by means of an infusion pump.

A further option is a composition which may be a powder or a liquid for the administration of the formulation in the form of a nasal or pulmonal spray. As a still further option, the formulation can also be administered transdermally, e.g. from a patch, optionally a iontophoretic patch, or transmucosally, e.g. bucally. The above-mentioned possible ways to administer the formulations of the invention are not to be considered as limiting the scope of the invention.

Of course, it is understood that depending on the peptide or peptides included in the formulations of the invention, the formulations may be used in methods of treatment of diseases or conditions for which use of the peptide is indicated. One skilled in the art would understand that when used in such methods of treatment, the formulations would have to be administered in amount effective to treat the condition or disease for which the peptide was being administered where an "effective amount" or an "amount . . . effective" is understood to mean a dosage which is sufficient in order for the treatment of the patient with the disease or condition to be treated to be effective compared to treatment without the administered dosage. It is to be understood that "an effective amount" is the effective dose to be determined by a qualified practitioner, who may titrate dosages to achieve the desired response. Factors for consideration of dose will include potency, bioavailability, desired pharmacokinetic/pharmacodynamic profiles, the condition or disease to be treated (e.g. diabetes, obesity, weight loss, gastric ulcers), patient-related factors (e.g. weight, health, age, etc.), presence of co-administered medications (e.g. insulin), time of administration, or other factors known to a medical practitioner.

The present invention also relates to a method for reducing deposits on production equipment during production of a peptide formulation, where the method comprises replacing the isotonicity agent previously utilized in said formulation with propylene glycol at a concentration of between 1-100 mg/ml.

In one embodiment, the reduction in deposits on the production equipment during production by the propylene glycol-containing formulation relative to that observed for the formulation containing the previously utilized isotonicity agent is measured by a simulated filling experiment as described in the Examples.

In another embodiment, the isotonicity agent to be replaced by propylene glycol is selected from the group consisting of sorbitol, sucrose, glycine, mannitol, lactose monohydrate, arginin, myo-inositol and dimethylsulfon.

In a further embodiment, the isotonicity agent previously utilized in said formulation is replaced with propylene glycol in a concentration of from about 1 to about 50 mg/ml.

In another embodiment, the isotonicity agent previously utilized in said formulation is replaced with propylene glycol in a concentration of from about 5 to about 25 mg/ml.

In yet another embodiment, the isotonicity agent previously utilized in said formulation is replaced with propylene glycol in a concentration of from about 8 to about 16 mg/ml.

In another embodiment of the invention, the propylene glycol-containing formulation has a pH in the range from about 7.0 to about 9.5.

In a further embodiment of the invention, the propylene glycol-containing formulation has a pH in the range from about 7.0 to about 8.0.

In yet a further embodiment of the invention, the propylene glycol-containing formulation has a pH in the range from 7.2 to about 8.0.

In a further embodiment of the invention, the propylene glycol-containing formulation has a pH in the range from about 7.0 to about 8.3.

In a further embodiment of the invention, the propylene glycol-containing formulation has a pH in the range from 7.3 to about 8.3.

The present invention also relates to a method for reducing deposits in the final product during production of a peptide formulation, where the method comprises replacing the isotonicity agent previously utilized in said formulation with propylene glycol at a concentration of between 1-100 mg/ml.

In one embodiment, the reduction in deposits in the final product is measured by a reduction in the number of vials and/or cartridges of the propylene glycol-containing formulation that must be discarded due to deposits relative to number of vials and/or cartridges of the formulation containing the previously utilized isotonicity agent that must be discarded due to deposits.

In another embodiment, the isotonicity agent to be replaced by propylene glycol is selected from the group consisting of sorbitol, sucrose, glycine, mannitol, lactose monohydrate, arginin, myo-inositol and dimethylsulfon.

In a further embodiment, the isotonicity agent previously utilized in said formulation is replaced with propylene glycol in a concentration of from about 1 to about 50 mg/ml.

In another embodiment, the isotonicity agent previously utilized in said formulation is replaced with propylene glycol in a concentration of from about 5 to about 25 mg/ml.

In yet another embodiment, the isotonicity agent previously utilized in said formulation is replaced with propylene glycol in a concentration of from about 8 to about 16 mg/ml.

In another embodiment of the invention, the propylene glycol-containing formulation has a pH in the range from about 7.0 to about 9.5.

In a further embodiment of the invention, the propylene glycol-containing formulation has a pH in the range from about 7.0 to about 8.0.

In yet a further embodiment of the invention, the propylene glycol-containing formulation has a pH in the range from 7.2 to about 8.0.

In a further embodiment of the invention, the propylene glycol-containing formulation has a pH in the range from about 7.0 to about 8.3.

In a further embodiment of the invention, the propylene glycol-containing formulation has a pH in the range from 7.3 to about 8.3.

The present invention further relates to a method for reducing the clogging of injection devices by a peptide formulation, where the method comprises replacing the isotonicity agent previously utilized in said formulation with propylene glycol at a concentration of between 1-100 mg/ml.

In one embodiment, the reduction in clogging of the injection device by the propylene glycol-containing formulation relative to that observed for the formulation containing the previously utilized isotonicity agent is measured in a simulated in use study as described in the Examples.

In another embodiment, the isotonicity agent to be replaced by propylene glycol is selected from the group consisting of inositol, maltose, glycine, lactose and mannitol.

In a further embodiment, the isotonicity agent previously utilized in said formulation is replaced with propylene glycol in a concentration of from about 1 to about 50 mg/ml.

In another embodiment, the isotonicity agent previously utilized in said formulation is replaced with propylene glycol in a concentration of from about 5 to about 25 mg/ml.

In yet another embodiment, the isotonicity agent previously utilized in said formulation is replaced with propylene glycol in a concentration of from about 8 to about 16 mg/ml.

In another embodiment of the invention, the propylene glycol-containing formulation has a pH in the range from about 7.0 to about 9.5.

In a further embodiment of the invention, the propylene glycol-containing formulation has a pH in the range from about 7.0 to about 8.0.

In yet a further embodiment of the invention, the propylene glycol-containing formulation has a pH in the range from 7.2 to about 8.0.

All scientific publications and patents cited herein are specifically incorporated by reference. The following examples illustrate various aspects of the invention but are in no way intended to limit the scope thereof.

EXAMPLES

Example 1

As laboratory experiments have shown that with regards to clogging of needles and deposits on needles, formulations without peptide ("placebo") give the same conclusions as formulations with peptide at 0.3-5.0 mg/ml, the screening studies in Example 1 have been done using placebo except where indicated otherwise.

Preparation of Formulations with Different Isotonic Agents

Preservative (5.5 mg/ml phenol) and buffer 1.24 mg/ml disodium hydrogen phosphate, dihydrate) were dissolved in water and the isotonic agent was added while stirring. pH was adjusted to pH 7.9 using Sodium Hydroxide and/or Hydrochloric acid. Finally, the formulation was filtered through a 0.22 μm filter. The isotonic agents tested in each formulation and their concentrations are shown in Table 1.

TABLE 1

Composition of the tested formulations

| Formulation no. | Tonicity modifier |
|---|---|
| 1 | Glucose monohydrate (38.0 mg/ml) |
| 2 | Laktose monohydrate (65.0 mg/ml) |
| 3 | Maltose (67.2 mg/ml) |
| 4 | Glycine (15.1 mg/ml) |
| 5 | Polyethylenglycol 400 (77.5 mg/ml) |
| 6 | L-arginin (24.6 mg/ml) |
| 7 | Myo-Inositol (35.2 mg/ml) |
| 8 | Propylene glycol (13.7 mg/ml) |
| 9 | Dimethylsulfon (18 mg/ml) |
| 10 | Mannitol (35.9 mg/ml) |
| 11 | Sorbitol (39.5 mg/ml) |
| 12 | Xylitol (39.5 mg/ml) |
| 13 | Sucrose (79.1 mg/ml |
| 14 | Glycerol (16 mg/ml) |

Osmolarity

The osmolarity of the different placebo formulations was determined and the results are shown in Table 2.

An isotonic solution has an osmolarity of around 0.286 osmol/L. As can be seen from Table 2 three of the formulations (PEG 400, sucrose and xylitol) are more than 20% from being isotonic (0.229-0.343 osmol/l), however for these kind of experiments the osmolarity is not expected to influence the results, though, the tonicity of the formulations should be adjusted in future experiments.

TABLE 2

The measured osmolarity of the formulations

| Formulation no. | Isotonic agent | Osmolarity |
|---|---|---|
| 1 | Glucose monohydrate (38.0 mg/ml) | 0.315 |
| 2 | Laktose monohydrate (65.0 mg/ml) | 0.283 |
| 3 | Maltose (67.2 mg/ml) | 0.306 |
| 4 | Glycine (15.1 mg/ml) | 0.286 |
| 5 | Polyethylenglykol 400 (77.5 mg/ml) | 0.370 |
| 6 | L-arginin(24.6 mg/ml) | 0.318 |
| 7 | Myo-Inositol (35.2 mg/ml) | 0.285 |
| 8 | Propylene glycol (13.7 mg/ml) | 0.268 |
| 9 | Dimethylsulfon (18 mg/ml) | 0.274 |
| 10 | Mannitol (35.9 mg/ml) | 0.284 |
| 11 | Sorbitol (39.5 mg/ml) | 0.310 |
| 12 | Xylitol (39.5 mg/ml) | 0.351 |
| 13 | Sucrose (79.1 mg/ml | 0.346 |
| 14 | Glycerol (16 mg/ml) | 0.262 |

Drop Test

A droplet of each formulation is placed on a microscope slide and let to dry. The deposit is visually examined by eye and light microscope.

A photograph of the dried droplets of some of the formulations is shown in FIG. 1. In this figure it is clearly observed that mannitol cause deposits on the microscope slide when let to dry. No deposits were observed for sorbitol, xylitol, sucrose and glycerol. The droplet on the far right (Form 1) contains mannitol and $Arg^{34}$, $Lys^{26}(N^{\epsilon}\text{-}(\gamma\text{-}Glu(N^{\alpha}\text{-hexadecanoyl})))$-GLP-1(7-37).

Figure 2:
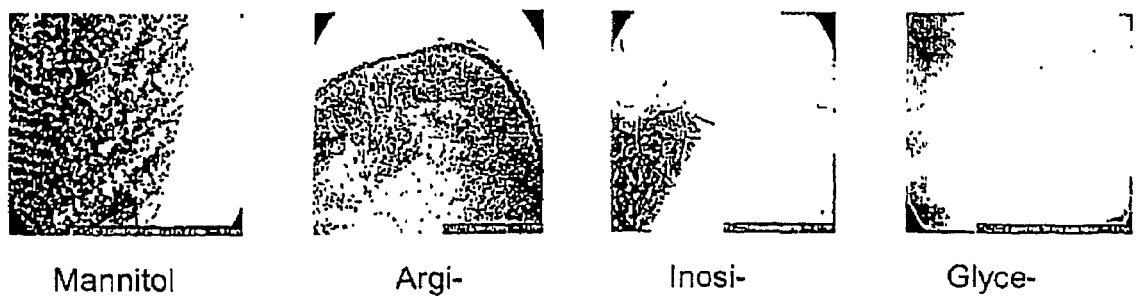
FIG. 2 shows light microscopy pictures of from left to right, some of the dried droplets of placebo formulations containing mannitol, arginin, inositol or glycerol as the isotonic agent.

In FIG. 2 the candidates causing the most deposits on the microscope slide are shown. For comparison glycerol, which does not cause deposits, is shown (mannitol, arginine, inositol).

Clogging Test

In this test 10 NOVOPENS® 1.5 ml mounted with NOVOFINE 30® G (G 30 needle) were tested for each formulation, 5 of them placed in upright and 5 in horizontal position. The Pensystems were stored at room temperature in between testing. Each day the needle was examined for deposits and an air shot was performed prior to injection into a tissue. Degree of resistance and clogging, if any, was noted. Injections were made on a daily basis with the same needle, and this was done for 9 working days for all the formulations.

The results from the clogging test are shown in Table 3.

three categories. 1. Those isotonic agents that do not cause deposits on the filling equipment: Xylitol, glycerol, glucose monohydrate, maltose, PEG 400 and propylene glycol. 2. Those isotonic agent that cause few deposits and have superior filling properties compared to mannitol: Sorbitol, sucrose and glycine. 3. Those isotonic agent that are comparable or worse than mannitol: Mannitol, lactose monohydrate, arginin, myo-inositol and dimethylsulfon.

Conclusion

In the simulated filling experiment xylitol, glycerol, glucose, maltose, PEG 400, propylene glycol, sorbitol, sucrose and glycine were found to be suitable replacements candidates for mannitol. However, as glucose is a reducing saccharide, and therefore is able to initiate unwanted degradation in the formulation, this tonicity modifier is ruled out. Furthermore, maltose is ruled out due to clogging of needles. This leads to the following candidates: glycerol, xylitol, sorbitol, sucrose, glycine, propylene glycol and PEG 400, which are found to have suitable properties as replacements candidates

TABLE 3

Clogging test in NovoPen 1.5 using 30G NovoFine

| Isotonic agent (no. of observations) | Some resistance | Resistance | Much resistance | Clogged | Drop at top of needle | Dried drop at needle top | Gel-like drop on needle | Deposits on needle |
|---|---|---|---|---|---|---|---|---|
| Mannitol (90) | 10 | 0 | 0 | 0 | 0 | 2 | 0 | 43 |
| Glycerol (90) | 13 | 0 | 0 | 0 | 1 | 0 | 3 | 0 |
| Sucrose (90) | 23 | 0 | 0 | 0 | 0 | 0 | 21 | 0 |
| Propylene glycol (90) | 20 | 0 | 0 | 0 | 0 | 0 | 0 | 0 |
| PEG 400 (90) | 25 | 1 | 0 | 0 | 12 (5 at needle) | 0 | 0 | 0 |
| arginin (90) | 26 | 2 | 0 | 0 | 3 (2 at needle) | 1 | 0 | 0 |
| Xylitol (90) | 14 | 0 | 0 | 0 | 5 | 0 | 0 | 0 |
| Dimethylsulfon (90) | 21 | 0 | 0 | 0 | 4 | 0 | 0 | 0 |
| sorbitol (90) | 12 | 0 | 0 | 0 | 9 | 1 | 0 | 1 |
| Myo-inositol (90) | 20 | 1 | 2 | 6 | 6 | 0 | 0 | 47 |
| Glucose (90) | 32 | 11 | 5 | 0 | 16 (7 at needle) | 1 | 0 | (1 at needle) |
| glycine (90) | 41 | 9 | 2 | 0 | 1 (2 at needle) | 0 | 0 | 31 (2 at needle) |
| maltose (90) | 35 | 8 | 7 | 4 | 16 (6 at needle) | 0 | 0 | 1 (5 at needle) |
| laktose (90) | 44 | 10 | 8 | 0 | 5 | 0 | 0 | 31 (2 at needle) |

Figure 3:
FIG. 3 shows light microscopy pictures of clogged needles dosed with placebo formulations containing myoinositol, maltose or glycerol as the isotonic agent.
Figure 3:
Figure 3:
Figure 4:
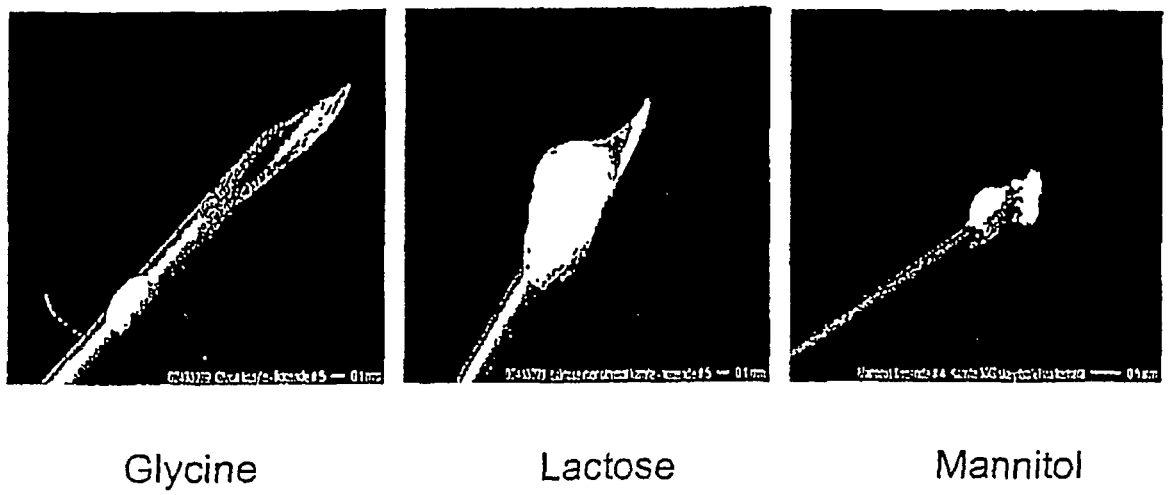
FIG. 4 shows light microscopy pictures of deposits on needles dosed with placebo formulations containing glycine, lactose or mannitol as the isotonic agent.
Figure 5:
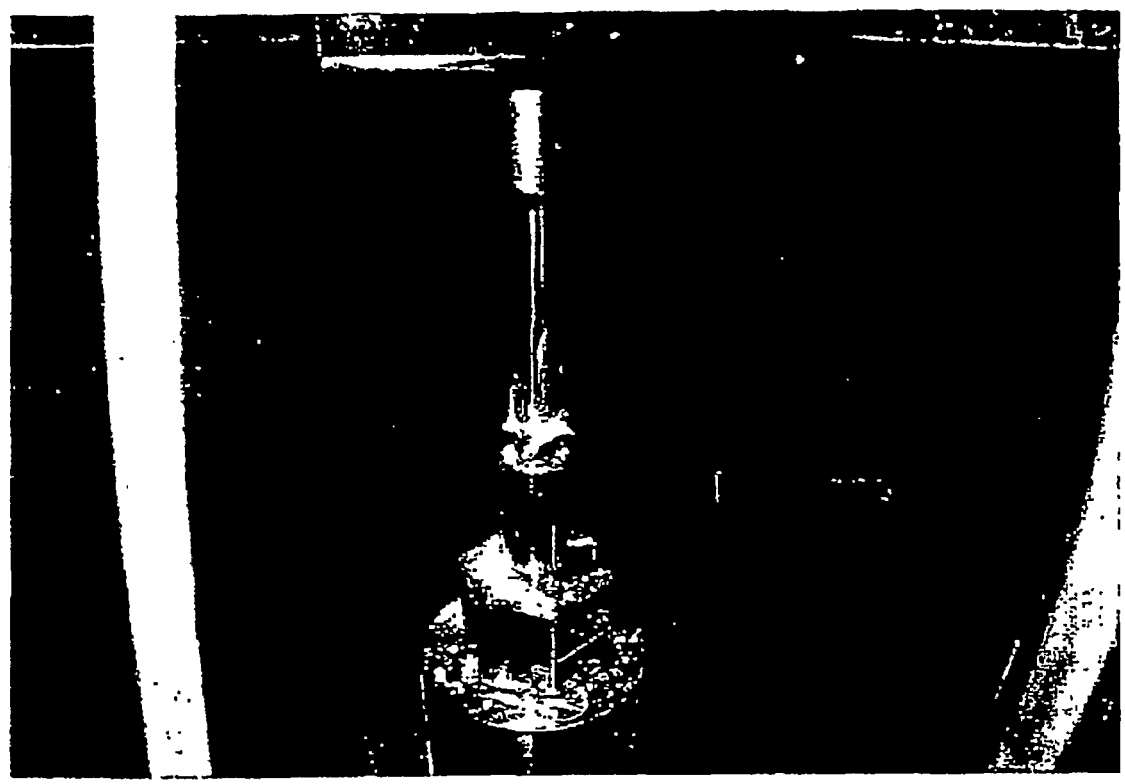
FIG. 5 shows filling equipment after 24 hours simulated filling with Arg$^{34}$, Lys$^{26}$(N$^{\epsilon}$-(γ-Glu(N$^{\alpha}$-hexadecanoyl)))-GLP-1(7-37) medium containing myo-inositol.

In Table 3 and in FIG. 3 it was observed that inositol and maltose clogged the needle. For comparison glycerol which does not clog the needle is shown in FIG. 3. In FIG. 4, and in Table 3, it was observed that formulations containing glycine, lactose and mannitol gave rise to a lot of deposits on the needle. For glycine, the deposits were a droplet deposited down the needle, whereas for lactose and mannitol the deposits occurred at the top of the needle.

Simulated Filling

1 L of each formulation was subjected to a simulated filling experiment which lasted for 24 hours. After 24 hours the filling equipment was inspected for the presence of deposits.

Based on the results from the simulated filling studies (data not shown), the placebo formulations can be divided into for mannitol in peptide formulations with regards to drop test, clogging of needles and simulated filling.

However, on the basis of the following considerations, propylene glycol was chosen as the isotonic agent over the other candidates to be further investigated in head to head comparison studies with mannitol:

a. propylene glycol was observed to have no influence on the physical and chemical stability of $Arg^{34}$, $Lys^{26}(N^{\epsilon}\text{-}(\gamma\text{-}Glu(N^{\alpha}\text{-hexadecanoyl})))$-GLP-1(7-37)-containing formulations;

b. propylene glycol was observed to have no influence on antimicrobial preservative testing; and c. use of propylene glycol would no require that further toxicity studies be tested

Example 2

Comparison of Mannitol and Propylene Glycol-Containing Placebo Formulations in Simulated Filling Studies and Simulated Use Studies Preparation of Formulations Preservative and buffer were dissolved in water and the isotonic agent was added while stirring. pH was adjusted to the aimed pH using Sodium Hydroxide and/or Hydrochloric acid. Finally, the formulation was filtered through a 0.22 μm filter. The compositions of the formulations were as follows:

Disodium hydrogen phosphate, dihydrate: 1.42 mg/ml
Phenol: 5.5 mg/ml
Propylene glycol or mannitol: 13.7 or 35.9 mg/ml
Water for Injection: up to 1.0 ml.
pH: 7.90

Simulated Filling Study

Figure 6:
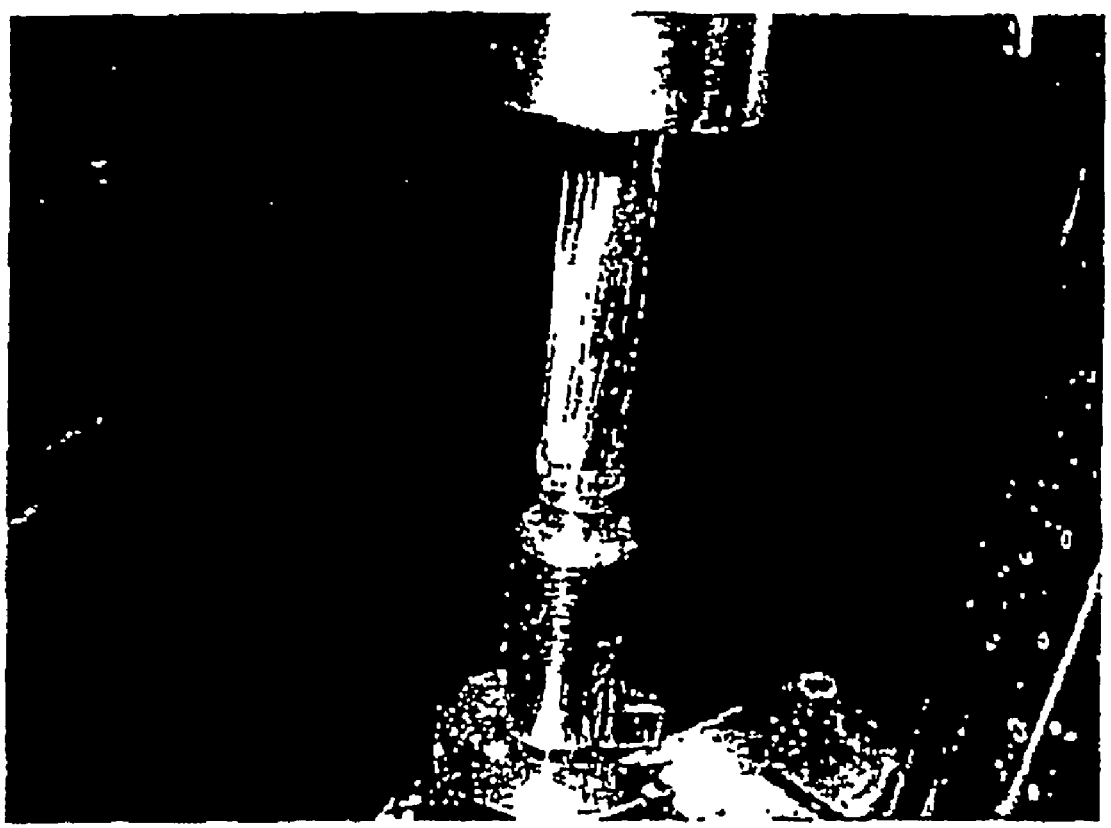
FIG. 6 shows deposits on filling equipment after 24 hours simulated filling with a mannitol-containing placebo formulation.

A simulated filling study lasting 24 hours was performed as described in Example 1 and after 24 hours, the filling equipment was inspected for the presence of deposits. No deposits were observed on the filling equipment for the propylene glycol formulation. By comparison, after 24 hours, a lot of deposits were observed on the filling equipment for the mannitol formulation (see FIG. 6).

Simulated in Use Study

Figure 7:
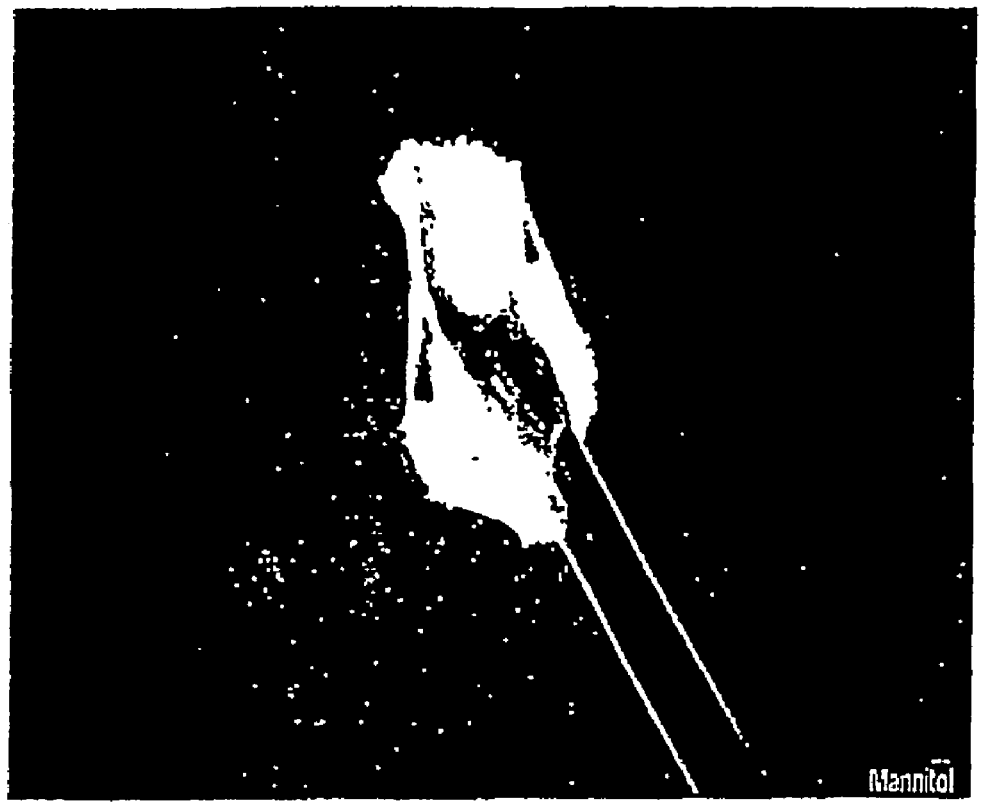
FIG. 7 shows deposits on needles dosed with mannitol (top panel) and propylene glycol (bottom panel)-containing Arg$^{34}$, Lys$^{26}$(N$^{\epsilon}$-(γ-Glu(N$^{\alpha}$-hexadecanoyl)))-GLP-1(7-37) formulations.
Figure 7:
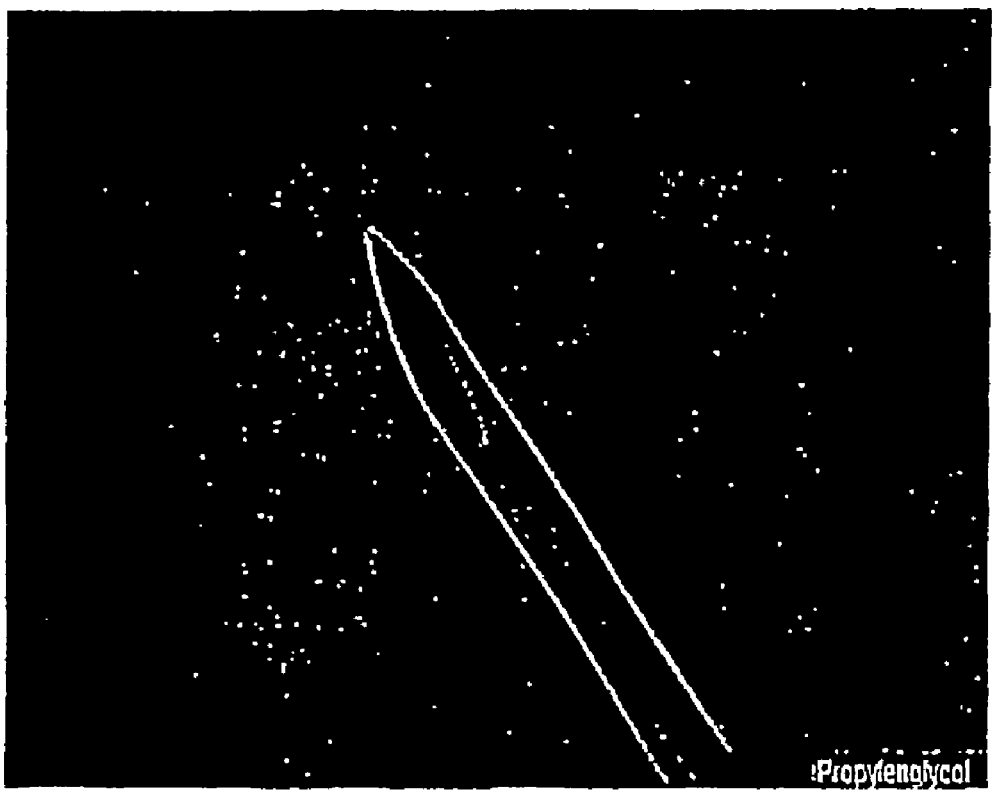

For the simulated in use study, a clogging test was conducted as described in Example 1. The same needle was used during the study period of ten working days and each day, the needle was inspected for the presence of deposits. FIG. 7 shows photographs of needles dosed with the propylene glycol (top panel) or mannitol (bottom panel) containing formulations. Deposits on the needle were observed in 48% of the cases when mannitol was used as an isotonic agent whereas no deposits were observed when propylene glycol was used as the isotonic agent.

Example 3

Comparison of Propylene Glycol to Mannitol in $Arg^{34}$, $Lys^{26}$ ($N^{\epsilon}$-($\gamma$-Glu($N^{\alpha}$-hexadecanoyl)))-GLP-1(7-37) Containing Formulations Preparation of Formulations Preservative, isotonic agent (mannitol or propylene glycol) and buffer were dissolved in water and pH was adjusted to the desired pH. $Arg^{34}$, $Lys^{26}$($N^{\epsilon}$-($\gamma$-Glu($N^{\alpha}$-hexadecanoyl)))-GLP-1(7-37) was dissolved in water while stirring slowly. The two solutions were then mixed and pH adjusted to the desired pH using sodium hydroxide and/or hydrochloric acid. Finally, the formulation was filtered through a 0.22 μm filter. The compositions of the formulations were as follows:

$Arg^{34}$, $Lys^{26}$($N^{\epsilon}$-($\gamma$-Glu($N^{\alpha}$-hexadecanoyl)))-GLP-1(7-37) (6.25 mg/ml),
Disodium hydrogen phosphate, dihydrate (1.42 mg/ml),
Phenol (5.5 mg/ml),
mannitol or propylene glycol (35.9 or 14.0 mg/ml),
Water for Injection (up to 1.0 ml),
pH: 8.15

Simulated in Use Study

For the simulated in use study, a clogging test was conducted as described in Example 1 except that a G31 needle was used. The same G31 needle was used during the study period of ten working days and each day, the needle was inspected for the presence of deposits. FIG. 7 shows photographs of needles with no deposits when dosed with the propylene glycol (bottom panel) or showing deposits when dosed with the mannitol (top panel) containing formulations.

For the mannitol containing formulation, clogging of the needle was observed in 1 out of 10 cases on day 4, 2 out of 10 cases on day 5, 3 out of 10 cases on day 8 and 4 out of 10 cases on day 9. By comparison, no clogging of needles was observed for the propylene glycol containing formulation.

It is believed that similar results to those obtained with the above-described propylene glycol-containing formulation would also be obtained if the pH was adjusted to 7.40, 7.70 or 7.90. In addition, additional formulations which could be tested include those having the following compositions:

Buffering agents: glycylglycine (1.32 mg/ml), L-Histidine (1.55 mg/ml), Hepes (2.38 mg/ml), or bicine (1.63 mg/ml)
Preservatives: phenol (5.0 or 5.5 mg/ml), benzylalcohol (18 mg/ml) or a mixture of m-cresol and phenol (2.5/2.0 mg/ml)
Propylene glycol: 14.0 or 14.3 mg.ml
Water for injection: up to 1.0 ml
pH: 7.40, 7.70, 7.90 or 8.15

Example 4

Influence of Peptide Concentration on Clogging of Needles $Arg^{34}$, $Lys^{26}$($N^{\epsilon}$-($\gamma$-Glu($N^{\alpha}$-hexadecanoyl)))-GLP-1(7-37) formulations were prepared as described in Example 3 using peptide concentrations ranging from 0-5 mg/ml of $Arg^{34}$, $Lys^{26}$($N^{\epsilon}$-($\gamma$-Glu($N^{\alpha}$-hexadecanoyl)))-GLP-1(7-37). The compositions of the formulations were as follows:

Liraglutide: 0, 0.3, 3 and 5 mg/ml
Disodium hydrogen phosphate, dihydrate: 0.71 mg/ml
Sodium dihydrogenphosphate, dihydrate: 0.62 mg/ml
Mannitol: 36.9 mg/ml
Phenol: 5.0 mg/ml
Water for injection: up to 1.0 ml
pH 7.40

A simulated in use study was conducted as in Example 3 except that a G30 needle was used and the results (data not shown) indicated that the clogging effect of the mannitol-containing formulations relative to the absence of clogging with the propylene glycol formulations was observed independent of the peptide concentration.

Example 5

Clogging of Needles in Lys β29 (Nε-tetradecanoyl) des(B30) Human Insulin and NovoMix 30 Formulations Containing Mannitol Preparation Of Formulations The Lys β29 (Nε-tetradecanoyl) des(B30) human insulin-containing formulation was prepared as follows:

a) Prepared a first solution by dissolving buffer, sodium chloride, preservatives (phenol and m-cresol) and mannitol in water b) Prepared a second solution of Lys β29 (Nε-tetradecanoyl) des(B30) human insulin and zinc acetate dissolved in water c) added the peptide-containing solution of step b) to the solution of step a); and d) adjusted the pH of the solution to the desired pH The composition of Lys β29 (Nε-tetradecanoyl) des(B30) human insulin-containing formulation prepared in the above manner was as follows:

Lys β29 (Nε-tetradecanoyl) des(B30) human insulin (2400 nmol), Phenol (1.80 mg/ml), m-cresol (2.06 mg/ml), Mannitol (30.0 mg/ml), disodiumphosphate, dihydrate (0.890 mg/ml), Sodium chloride (1.17 mg/ml), Zinc acetate (65.4 ug/ml), water for injection (up to 1.0 ml), pH: 7.4

The NOVOMIX® 30-containing formulation was prepared as follows:
a) Prepared a solution by dissolving buffer, sodium chloride, phenol, mannitol and sodium hydroxide in water
b) Prepared a solution of sodium chloride, phenol and mannitol in water
c) Prepared a solution of protamine sulphate in water
d) Prepared a solution of insulin, hydrochloric acid and zinc in water
e) Solutions b), c) and d) were mixed
f) Solution e) was added to the solution of step a)
g) Adjusted the pH of the solution to the desired pH and crystallized at room temperature
h) Prepared a solution by dissolving m-cresol, phenol and mannitol in water
i) Solution h) is added to the crystalline fraction of step g); and
j) Adjusted the pH to the desired pH The composition of the NOVOMIX® 30-containing formulation prepared in the above manner was as follows:

Insulin aspart (100 units/ml), protamine sulphate (approx. 0.33 mg/ml), phenol (1.50 mg/ml), m-cresol (1.72 mg/ml), mannitol (30.0 mg/ml), disodiumphosphate dihydrate (1.25 mg/ml), sodium chloride (0.58 mg/ml), zinc (19.6 ug/ml), water for injection (up to 1.0 ml), pH: 7.3.

Results

A simulated in use study was conducted as described in Example 3 using G31 needles where 20 needles were investigated for 10 days. The results were as follows: Clogging of needles was observed for Lys β29 (Nε-tetradecanoyl) des(B30) human insulin on day 2 (5%), day 3 (70%) and on day 4 (100%). Clogging of needles for NovoMix 30 was observed on day 3 (5%), day 4 (10%), day 5 (35%), day 6 (40%), day 8 (50%), day 9 (55%) and day 10 (80%). Thus, the effect of mannitol on the clogging of needles is independent of the type of peptide included in the formulations since a comparable clogging effect was observed with $Arg^{34}$, $Lys^{26}(N^{\epsilon}$-(γ-Glu($N^{\alpha}$-hexadecanoyl)))-GLP-1(7-37), Lys β29 (Nε-tetradecanoyl) des(B30) human insulin and NovoMix 30.

Example 6

Testing of Lys β29 (Nε-tetradecanoyl) des(B30) human insulin and NOVOMIX® 30 formulations containing propylene glycol The preparation and composition of the Lys β29 (Nε-tetradecanoyl) des(B30) human insulin and NOVOMIX® 30 formulations will be as described in Example 5 except that mannitol will be replaced with a concentration of propylene glycol that assures tonicity. A simulated in use test will then be conducted as described in Example 5.

Based on the fact that the clogging effect of Lys β29 (Nε-tetradecanoyl) des(B30) human insulin and NOVOMIX® 30 mannitol-containing formulations was similar to that observed with $Arg^{34}$, $Lys^{26}(N^{\epsilon}$-(γ-Glu($N^{\alpha}$-hexadecanoyl)))-GLP-1(7-37) mannitol-containing formulations, it is believed that the effect of propylene glycol on the clogging effect of Lys β29 (Nε-tetradecanoyl) des(B30) human insulin and NovoMix 30-containing formulations will be similar to that observed with $Arg^{34}$, $Lys^{26}(N^{\epsilon}$-(γ-Glu($N^{\alpha}$-hexadecanoyl)))-GLP-1(7-37)-containing formulations.

---

---

The invention claimed is:

1. A pharmaceutical formulation comprising at least one GLP-1 agonist, a disodium phosphate dihydrate buffer and propylene glycol, wherein said propylene glycol is present in said formulation in a final concentration of from about 1 mg/ml to about 100 mg/ml and wherein said formulation has a pH of from about 7.0 to about 10.0.

2. The formulation according to claim 1, wherein the concentration of propylene glycol is from about 1 mg/ml to about 50 mg/ml.

3. The formulation according to claim 1, wherein the concentration of propylene glycol is from about 5 mg/ml to about 25 mg/ml.

4. The formulation according to claim 1, wherein the concentration of propylene glycol is from about 8 mg/ml to about 16 mg/ml.

5. The formulation according to claim 1, wherein the pH of said formulation is about 7.0 to about 9.5.

6. The formulation according to claim 1, wherein the pH of said formulation is about 7.0 to about 8.3.

7. The formulation according to claim 1, wherein the pH of said formulation is about 7.3 to about 8.3.

8. The formulation according to claim 1, further comprising a preservative.

9. The formulation according to claim 8, wherein said preservative is present in a concentration from 0.1 mg/ml to 20 mg/ml.

10. The formulation according to claim 1, wherein said GLP-1 agonist is selected from the group consisting of GLP-1(7-36)-amide, GLP-1(7-37), a GLP-1(7-36)-amide analogue, a GLP-1(7-37) analogue, or a derivative of any of these.

11. The formulation according to claim 10, wherein said GLP-1 agonist is a derivative of GLP-1(7-36) or GLP-1(7-37) or a GLP-1(7-36)-amide analogue or a GLP-1(7-37) analogue, where said derivative has a lysine residue and a lipophilic substituent attached with or without a spacer to the epsilon amino group of said lysine.

12. The formulation according to claim 11, wherein said lipophilic substituent has from 8 to 40 carbon atoms.

13. The formulation according to claim 12, wherein said spacer is an amino acid.

14. The formulation according to claim 13, wherein said GLP-1 agonist is $Arg^{34}$, $Lys^{26}$(N-ε-(γ-Glu(N-α-hexadecanoyl)))-GLP-1(7-37).

15. The formulation according to claim 1, wherein said GLP-1 agonist is selected from the group consisting of $Gly^8$-GLP-1(7-36)-amide, $Gly^8$-GLP-1(7-37), $Val^8$-GLP-1(7-36) amide, $Val^8$-GLP-1(7-37), $Val^8Asp^{22}$-GLP-1(7-36)-amide, $Val^8Asp^{22}$-GLP-1(7-37), $Val^8Glu^{22}$-GLP-1(7-36)-amide, $Val^8Glu^{22}$-GLP-1(7-37), $Val^8Lys^{22}$-GLP-1(7-36)-amide, $Val^8Lys^{22}$-GLP-1(7-37), $Val^8Arg^{22}$-GLP-1(7-36)-amide, $Val^8Arg^{22}$-GLP-1(7-37), $Val^8His^{22}$-GLP-1(7-36)-amide, $Val^8His^{22}$-GLP-1(7-37), $Arg^{34}$GLP-1(7-37), $Arg^{26,34}Lys^{36}$GLP-1(7-36), $Arg^{26}$GLP-1(7-37), and $Gly^8$, $Arg^{26,34}Glu^{37}Lys^{38}$GLP-1(7-38) and derivatives of any of these.

16. A method of preparing a GLP-1 agonist formulation suitable for use in an injection device, said method comprising preparing a formulation containing a GLP-1 agonist, propylene glycol, a disodium phosphate dihydrate buffer, and a preservative, wherein said propylene glycol is present in a concentration from about 1 mg/ml to about 100 mg/ml, and wherein said formulation has a pH from about 7.0 to about 10.0, and wherein said GLP-1 agonist, said propylene glycol and said buffer and preservative are mixed together to produce said formulation as follows:
   a) preparing a first solution by dissolving preservative, propylene glycol and buffer in water;
   b) preparing a second solution by dissolving the GLP-1 agonist in water;
   c) mixing the first and second solutions; and
adjusting the pH of the mixture in c) to a pH of from about 7.0 to about 10.0.

17. The method according to claim 16, wherein the concentration of propylene glycol is from about 1 mg/ml to about 50 mg/ml.

18. The method according to claim 16, wherein the concentration of propylene glycol is from about 5 mg/ml to about 25 mg/ml.

19. The method according to claim 16, wherein the concentration of propylene glycol is from about 8 mg/ml to about 16 mg/ml.

20. The method according to claim 16, wherein the pH of said formulation is about 7.0 to about 9.5.

21. The method according to claim 16, wherein the pH of said formulation is about 7.0 to about 8.0.

22. The method according to claim 16, wherein the pH of said formulation is about 7.2 to about 8.0.

23. A method for reducing deposits on production equipment during production of a GLP-1 agonist formulation, said method comprising replacing the isotonicity agent previously utilized in said formulation with propylene glycol at a concentration of between 1-100 mg/ml, and wherein said GLP-1 agonist formulation comprises a disodium phosphate dihydrate buffer.

24. The method according to claim 23, wherein the reduction in deposits on the production equipment during production by the propylene glycol-containing formulation relative to that observed for the formulation containing the previously utilized isotonicity agent is measured by a simulated filling experiment.

25. The method according to claim 23, wherein the isotonicity agent to be replaced by propylene glycol is selected from the group consisting of sorbitol, sucrose, glycine, mannitol, lactose monohydrate, arginin, myo-inositol and dimethylsulfon.

26. A method for reducing deposits in the final product during production of a GLP-1 agonist formulation, said method comprising replacing the isotonicity agent previously utilized in said formulation with propylene glycol at a concentration of between 1-100 mg/ml, and wherein said GLP-1 agonist formulation comprises a disodium phosphate dihydrate buffer.

27. The method according to claim 26, wherein the reduction in deposits in the final product is measured by a reduction in the number of vials and/or cartridges of the propylene glycol-containing formulation that must be discarded due to deposits relative to number of vials and/or cartridges of the formulation containing the previously utilized isotonicity agent that must be discarded due to deposits.

28. The method according to claim 26, wherein the isotonicity agent to be replaced by propylene glycol is selected from the group consisting of sorbitol, glycerol, sucrose, glycine, mannitol, lactose monohydrate, arginin, myo-inositol and dimethylsulfon.

29. A method for reducing the clogging of injection devices by a GLP-1 agonist formulation, said method comprising replacing the isotonicity agent previously utilized in said formulation with propylene glycol at a concentration of between 1-100 mg/ml, and wherein said GLP-1 agonist formulation comprises a disodium phosphate dihydrate buffer.

30. The method according to claim 29, wherein the reduction in clogging of the injection device by the propylene glycol-containing formulation relative to that observed for the formulation containing the previously utilized isotonicity agent is measured in a simulated in use study.

31. The method according to claim 29, wherein the isotonicity agent to be replaced by propylene glycol is selected from the group consisting of inositol, maltose, glycine, lactose and mannitol.

* * * * *